(12) United States Patent
Ibdah

(10) Patent No.: US 10,767,187 B2
(45) Date of Patent: Sep. 8, 2020

(54) **IDENTIFICATION AND CHARACTERIZATION OF UDP-GLUCOSE:PHLORETIN 4'-O-GLUCOSYL TRANSFERASE FROM *MALUS X DOMESTICA* BORKH**

(71) Applicant: The State of Israel, Ministry of Agriculture & Rural Development Agricultural Research Organization (ARO) (Volcani Center), Rishon-LeZion (IL)

(72) Inventor: Mwafaq Ibdah, Ramat-Yishai (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 0 days.

(21) Appl. No.: 16/082,623

(22) PCT Filed: Mar. 9, 2017

(86) PCT No.: PCT/IL2017/050310
§ 371 (c)(1),
(2) Date: Sep. 6, 2018

(87) PCT Pub. No.: WO2017/154009
PCT Pub. Date: Sep. 14, 2017

(65) Prior Publication Data
US 2019/0062768 A1    Feb. 28, 2019

Related U.S. Application Data

(60) Provisional application No. 62/305,591, filed on Mar. 9, 2016.

(51) Int. Cl.
| | | |
|---|---|---|
| *C12N 15/82* | (2006.01) | |
| *C12P 19/44* | (2006.01) | |
| *A61K 31/05* | (2006.01) | |

(52) U.S. Cl.
CPC ......... *C12N 15/8243* (2013.01); *A61K 31/05* (2013.01); *C12P 19/44* (2013.01)

(58) Field of Classification Search
None
See application file for complete search history.

(56) References Cited

U.S. PATENT DOCUMENTS

2011/0030098 A1    2/2011    Jugdé et al.

FOREIGN PATENT DOCUMENTS

| JP | 2006-262910 | 10/2006 |
|---|---|---|
| WO | WO 2009/082243 | 7/2009 |
| WO | WO 2017/154009 | 9/2017 |

OTHER PUBLICATIONS

Fischer et al (Flavonoid genes of pear (Pyrus communis). Trees. 21:521-529, 2007) (Year: 2007).*
Gosch et al (Cloning and heterologous expression of glycosyltransferases from Malus x domestica and Pyrus communis, which convert phloretin to phloretin 2'-O-glucoside (phloridzin). Plant Science 178. 299-306, 2010) (Year: 2010).*
Randey et al (Enzymatic Synthesis of Novel Phloretin Glucosides Applied and Environmental Microbiology p. 3516-3521, 2013), (Year: 2013).*
Hutabarat et al (Transgenic apple plants overexpressing the chalcone 3-hydroxylase gene of Cosmos sulphureus show increased levels of 3-hydroxyphloridzin and reduced susceptibility to apple scab and fire blight. Planta. 243:1213-1224, published online Feb. 2016). (Year: 2016).*
International Preliminary Report on Patentability dated Sep. 20, 2018 From the International Bureau of WIPO Re. Application No. PCT/IL2017/050310. (6 pages).
International Search Report and the Written Opinion dated May 29, 2017 From the International Searching Authority Re. Application No. PCT/IL2017/050310. (10 pages).
Duge de Bernonville et al. "Dihydrochalcones: Implication in Resistance to Oxidative Stress and Bioacitivies Against Advanced Glycation End-Products and Vasoconstriction", Phytochemistry, 71(4): 443-452, Available Online Dec. 21, 2009.
Fischer et al. "Flavonoid Genes of Pear (*Pyrus communis*)", Trees, 21(5): 521-529, Published Online Jun. 5, 2007. Table 1, Malus Sequence AY786997, P.521, Right Col., Last Para—p. 523, Left Col., First Para, p. 527, Left Col., Last Para, *Pyrus* (Pear) Sequence AY954922.
Gosch et al. "Cloning and Heterologous Expression of Glycosyltransferases From Malus x Domestica and Pyrus Communis, Which Convert Phloretin to Phloretin 2'-O-Glucoside (Phloridzin)", Plant Science, 178(3): 299-306, Available Online Jan. 8, 2010. p. 299, Last Para—p. 300, First Para, p. 302, Right Col., First Para, Figs.2, 4, Tables 2, 4.
Gosh et al. "Substrate Specificity and Contribution of the Glycosyltransferase UGT71A15 to Phloridzin Biosynthesis", Trees, 26(1): 259-271, Published Online Dec. 28, 2011.
Jugde et al. "Isolation and Characterization of a Novel Glycosyltransferase That Converts Phloretin to Phlorizin, a Potent Antioxidant in Apple", The FEBS Journal, 275(15):3804-3814, Aug. 2008.
Ono et al. "Yellow Flowers Generated by Expression of the Aurone Biosynthetic Pathways", Proc. Natl. Acad. Sci. USA, PNAS, 103(29): 11075-11080, Jul. 18, 2006.

(Continued)

*Primary Examiner* — Medina A Ibrahim
*Assistant Examiner* — Wayne Zhong

(57) ABSTRACT

A method of producing trilobatin is disclosed. The method comprising contacting a polypeptide comprising an amino acid sequence at least 90% identical to SEQ ID NO: 8 and having a 4'-O-glycosyltransferase activity with phloretin and UDP-glucose under conditions which allow the formation of trilobatin, thereby producing trilobatin. A method of producing a plant which produces trilobatin, transgenic plant or plant cell and methods of producing transgenic plants are disclosed. Composition comprising trilobatin are also disclosed.

7 Claims, 12 Drawing Sheets
(3 of 12 Drawing Sheet(s) Filed in Color)
Specification includes a Sequence Listing.

(56) References Cited

OTHER PUBLICATIONS

Pandey et al. "Enzymatic Synthesis of Novel Phloretin Glucosides", Applied and Environmental Microbiology, 79(11): 3516-3521, Published Online Mar. 29, 2013. p. 3516, Last Para—p. 3517, First Para, Figs.1, 4.

Yahyaa et al. "Identification and Characterization of Udp-Glucose: Phloretin 4'-O-Glycosyltransferase From Malus x Domestica Borkh", Phytochemistry, 130: 47-55, Available Online Jun. 14, 2016.

Supplementary European Search Report and the European Search Opinion dated Aug. 26, 2019 From the European Patents Office Re. Application No. 17762653.8. (10 pages).

Fischer et al. "Malus x Domestica UDP-Glucose:Flavonoid 7-0-Glucosyltransferase mRNA, Complete CDS", Database ENA [Online], XP002793546, Retrieved From EBI Accession No. EMBL:AY786997, Database Accession No. AY786997, Aug. 29, 2007.

Fischer et al. "Pyrus Communis UDP-Glucose:Flavonoid 7-0-Glucosyltransferase mRNA, Complete CDS", Database ENA [Online], XP002793547, Retrieved From EBI Accession No. EMBL:AY954922, Database Accession No. AY954922, Aug. 29, 2007.

\* cited by examiner

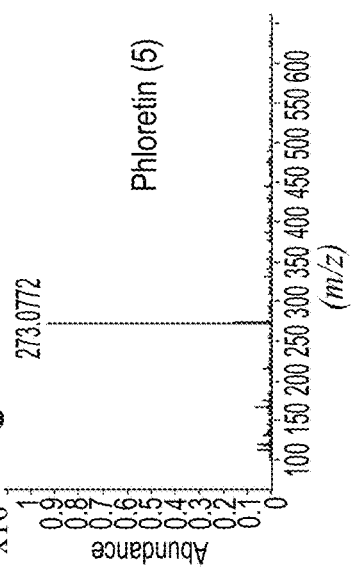
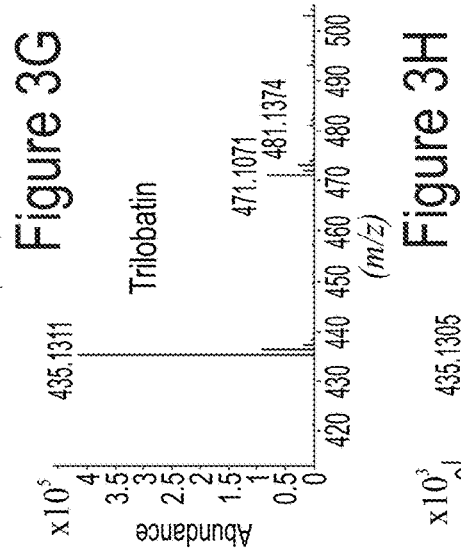
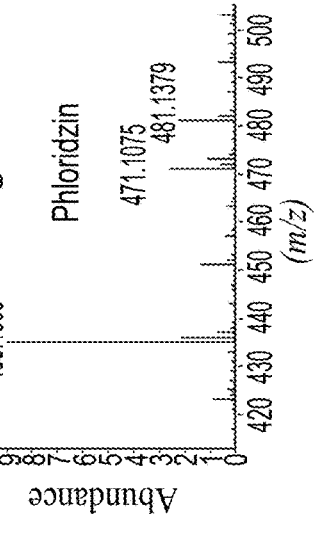
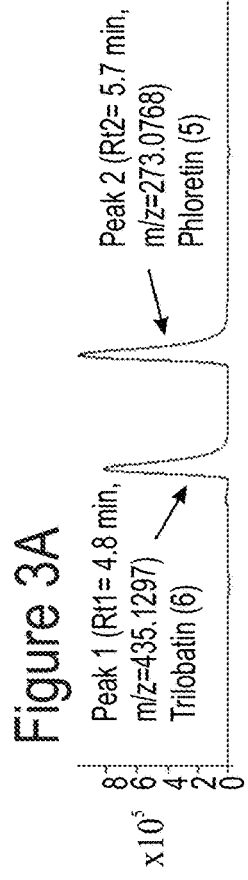
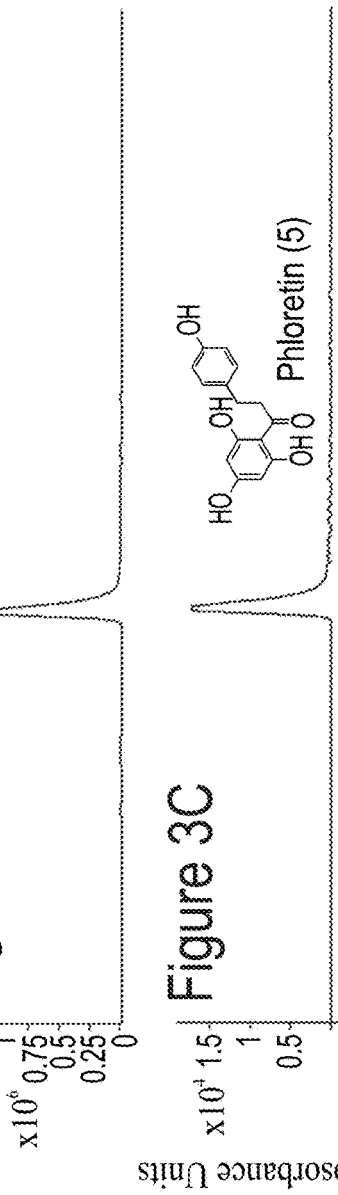
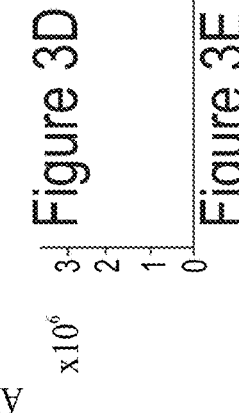
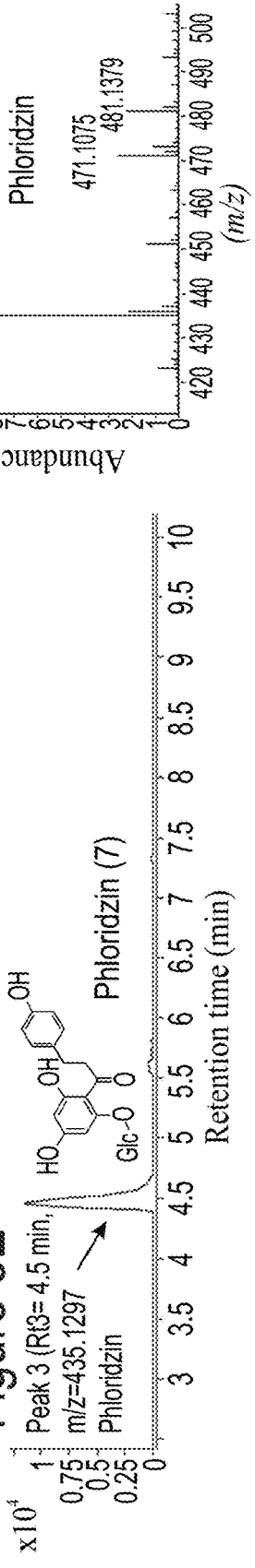

| Substrate | Structure | Conversion rate (%) |
|---|---|---|
| Phloretin (5) | 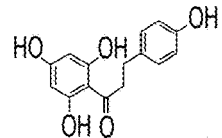 | 100 ± 5.8 |
| Trilobatin (6) | 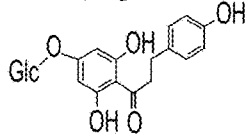 | 12 ± 1.7 |
| Phloridzin (7) | 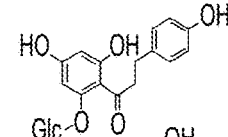 | 13 ± 1.2 |
| Quercetin (8) | 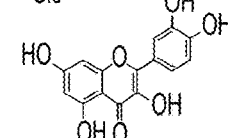 | 20 ± 1.1 |
| Naringenin (9) | 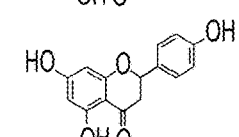 | 22 ± 2.0 |
| Epicatechin (10) | 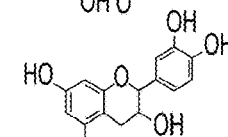 | 0 |
| Cyanidin (11) | 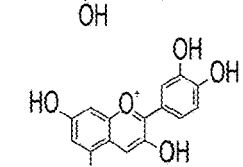 | 0 |
| 4-Coumaric acid (12) | 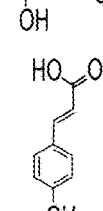 | 0 |
| Caffeic acid (13) | 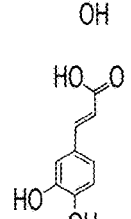 | 0 |
| Butein (14) | 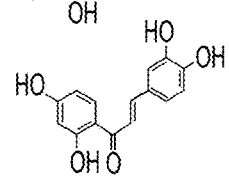 | 23 ± 3.4 |
Figure 4

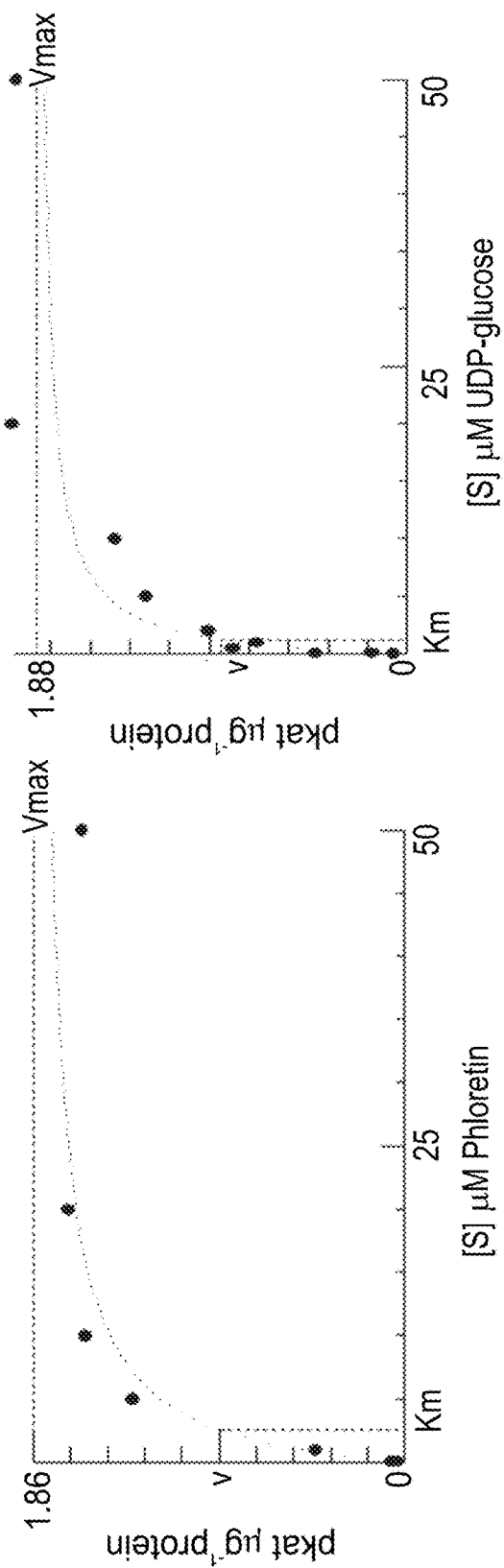
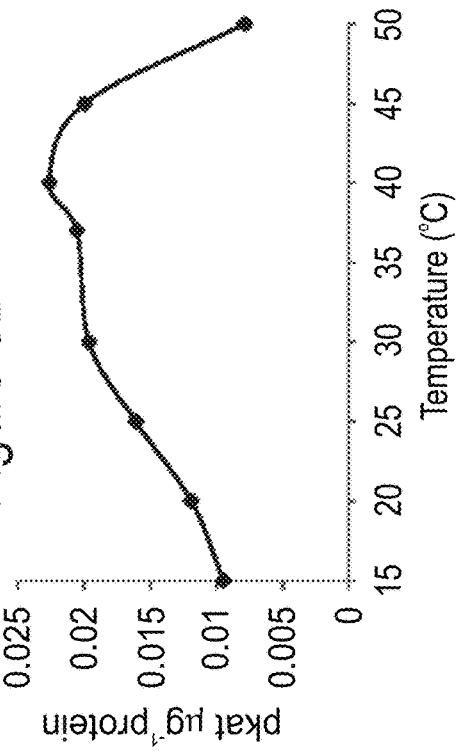
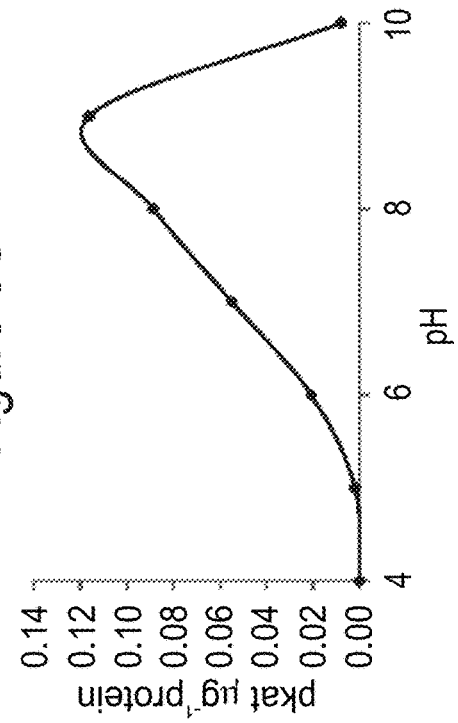
Figure 5A
Figure 5B
Figure 5C
Figure 5D

Figure 7

MdPh-4'-OGT (accession number AAX16493)

```
M V Q H R F L L V T F P A Q G H I N P S
L Q F A K R L I N T T G A H V T Y V T S
L S A H R R I G N G S I P D G L T Y A P
F S D G Y D D G F K P G D N V D D Y M S
E L R R R G V Q A I T D L V V A S A N E
G H P Y T C L V Y S L L P W S A G M A
H E L H L P S V L W I Q P A T V F D I
Y Y Y Y F N G Y K D L I R D N T S S G T
N N V L P C S I E L P G L P L S F T S R
D L P S F M V D T N P Y N F A L P L F Q
E Q M E L L E R E T N P T I L V N T F D
A L E P E A L K A I D K Y N L I G V G P
L I P S A F L D G K D P S D K S F G G D
L F Q K S D S S Y L E W L N S K P E G
S V I Y V S F G S I S V L G K A Q M E E
I A K G L L D C G L P F L W V I R D K V
G K K G D D N E A K E E E M L R C R E
E L E E L G M I V P W C S Q V E V L S S
P S L G C F V T H C G W N S S L E S L V
S G V P V V A F P Q W T D Q G T N A K L
I E D Y W K T G V R V T P N E E G I V T
G E E L K R C L D L V L G S G E I G E D
V R R N A K K W K D L A R E A V S E G D
S S D K N L R A F L D Q I K V L K D A R
H
```

SEQ ID NO: 8

ATGGTGCAACACCGCTTTCTACTCGTCACATTTCCAGCTCAAGGCCACATCAACCCTTCC
CTCCAATTCGCCAAGCGCCTTATCAACACTACAGGTGCGCATGTCACCTACGTTACTAGT
CTGTCAGCCCATCGCCGTATAGGCAATGGCTCAATTCCAGATGGATTGACCTATGCGCCC
TTCTCTGATGGGTACGACGATGGGTTTAAGCCCGGCGACAACGTCGACGACTACATGTCA
GAGCTGCGGCGCCGCGGAGTACAAGCCATTACCGACCTTGTAGTCGCAAGTGCAAACGAG
GGTCACCCTTACACTTGCCTAGTCTACTCATTACTTCTCCCTTGGTCGGCAGGGATGGCA
CATGAACTTCACCTCCCAAGCGTGCTGCTTTGGATTCAGCCAGCCACGGTTTTCGACATC
TACTACTATTACTTTAACGGGTACAAAGATCTCATCCGGGATAATACTAGTTCTGGTACG
AACAATGTCCTTCCATGTTCAATAGAATTACCAGGTTTGCCATTATCTTTCACAAGCCGA
GACCTTCCCTCCTTCATGGTGGATACAAATCCGTACAATTTCGCCCTCCCGTTGTTTCAA
GAACAGATGGAGCTGTTGGAAAGAGAAACCAATCCGACCATTCTAGTCAACACGTTCGAT
GCACTAGAGCCGGAAGCCTTAAAAGCAATTGACAAGTACAACTTGATTGGAGTTGGGCCA
TTGATTCCGTCCGCTTTCTTGGACGGCAAGGATCCATCGGACAAGTCATTTGGAGGCGAT
CTTTTCCAAAAATCAAAGGACTCTTCATACCTCGAGTGGCTGAACTCGAAGCCAGAAGGG
TCGGTGATTTATGTGTCCTTCGGAAGCATTTCTGTGTTGGGAAAGGCCCAAATGGAGGAA
ATCGCAAAAGGGTTGTTGGATTGCGGCCTTCCGTTCTTGTGGGTTATTAGAGATAAGGTC
GGCAAGAAGGGAGACGATAACGAGGCGAAGAAAGAAGAAGAGATGTTGAGGTGCAGAGAG
GAATTGGAAGAGCTCGGGATGATAGTGCCGTGGTGTAGTCAAGTGGAGGTTCTCTCTAGT
CCTTCGTTGGGTTGCTTTGTGACACATTGTGGGTGGAATTCAAGTTTGGAGAGCTTGGTT
TCAGGGGTGCCCGTGGTGGCGTTTCCTCAGTGGACGGACCAAGGGACGAATGCCAAGTTG
ATAGAGGACTATTGGAAGACAGGAGTGAGGGTGACACCAAATGAGGAGGGGATAGTTACG
GGTGAGGAGCTCAAGAGGTGCTTGGATTTGGTATTGGGAAGTGGGGAGATTGGTGAAGAC
GTGAGAAGGAATGCTAAGAAATGGAAAGATTTGGCAAGAGAGGCTGTGAGTGAAGGGGAC
TCTTCGGACAAGAATCTCAGGGCTTTCTTGGATCAGATCAAGGTTTTAAAAGATGCTAGG
CACTAG

SEQ ID NO: 7

Figure 8

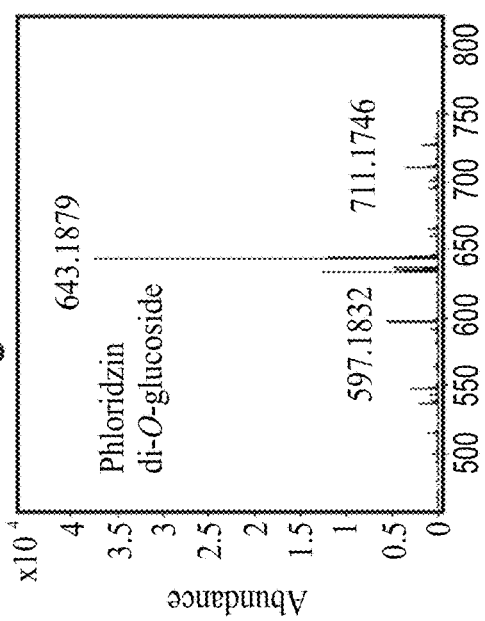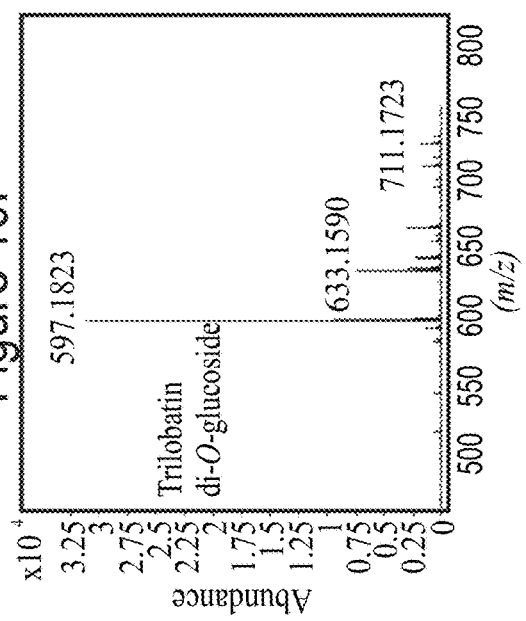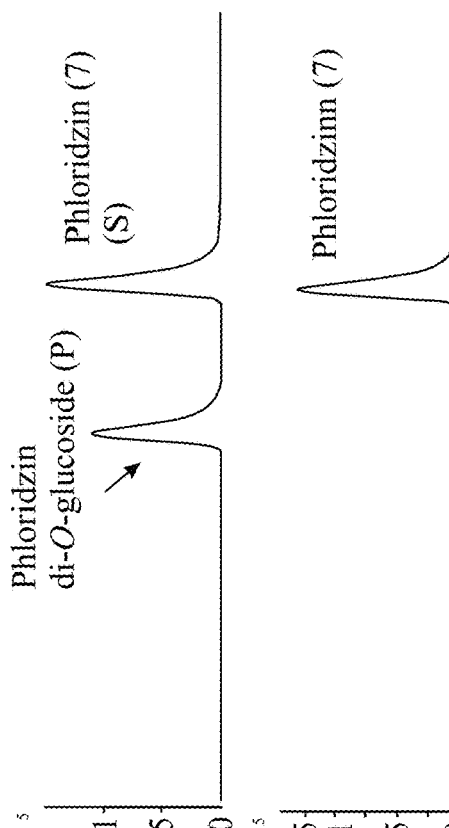
Figure 10A
Figure 10B
Figure 10C
Figure 10D
Figure 10E
Figure 10F

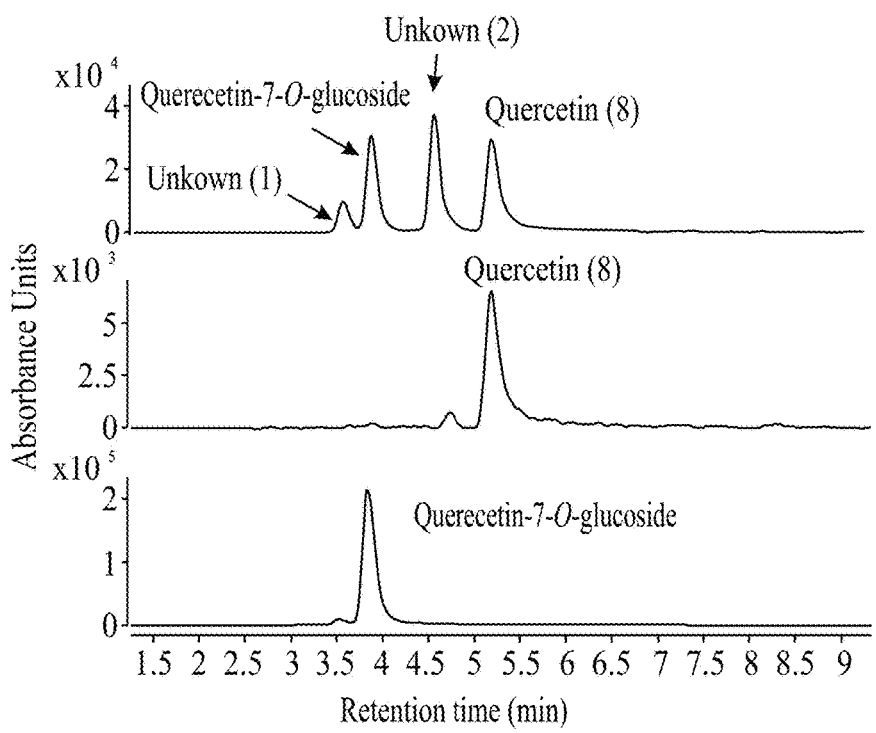
Figure 12A
Figure 12B
Figure 12C
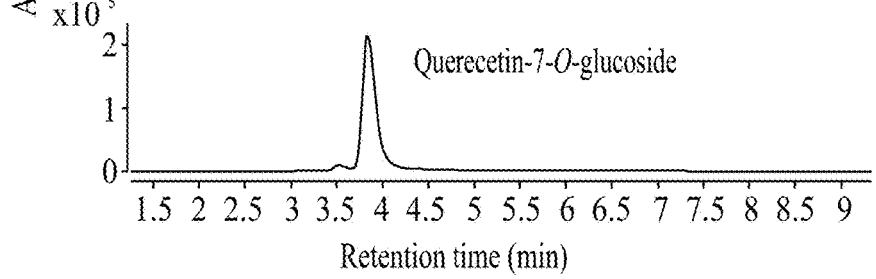
Figure 12D
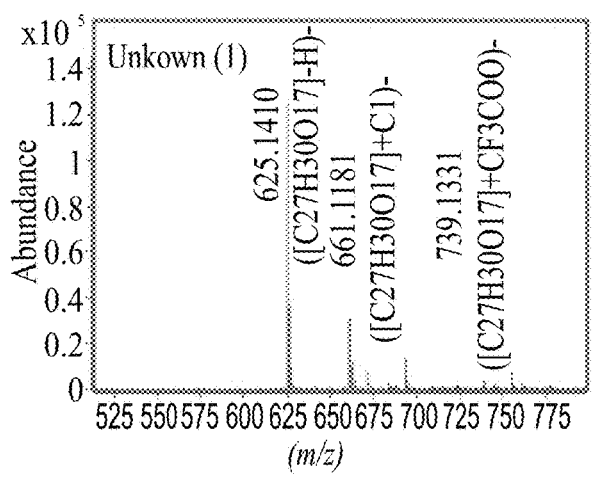
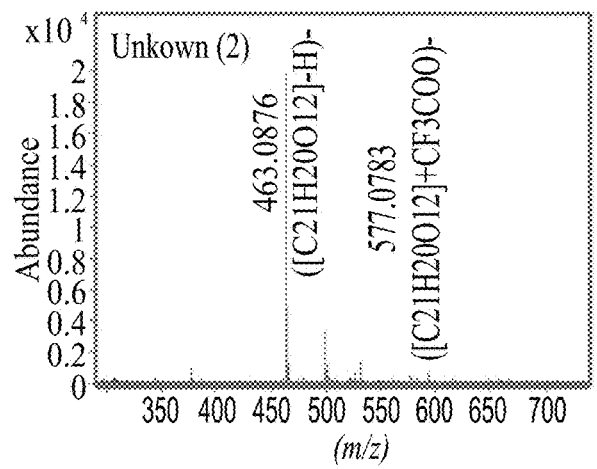

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
atggtgcaac accgctttct ac                                            22

<210> SEQ ID NO 2
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 2
gtgcctagca tcttttaaaa ccttgatctg                                    30

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
cgataacgag gcgaagaaag a                                             21

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
gagaacctcc acttgactac ac                                            22

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
tcgtccgtgg agaagagtta                                               20
```

<210> SEQ ID NO 6
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 6
aatcatggat ggctggaaga g                                            21

<210> SEQ ID NO 7
<211> LENGTH: 1446
<212> TYPE: DNA
<213> ORGANISM: Malus domestica

<400> SEQUENCE: 7
atggtgcaac accgctttct actcgtcaca tttccagctc aaggccacat caacccttcc    60
ctccaattcg ccaagcgcct tatcaacact acaggtgcgc atgtcaccta cgttactagt   120
ctgtcagccc atcgccgtat aggcaatggc tcaattccag atggattgac ctatgcgccc   180
ttctctgatg ggtacgacga tgggtttaag cccggcgaca acgtcgacga ctacatgtca   240
gagctgcggc gccgcggagt acaagccatt accgaccttg tagtcgcaag tgcaaacgag   300
ggtcacccct tacacttgcct agtctactca ttacttctcc cttggtcggc agggatggca   360
catgaacttc acctcccaag cgtgctgctt tggattcagc cagccacggt tttcgacatc   420
tactactatt actttaacgg gtacaaagat ctcatccggg ataatactag ttctggtacg   480
aacaatgtcc ttccatgttc aatagaatta ccaggtttgc cattatcttt cacaagccga   540
gaccttccct ccttcatggt ggatacaaat ccgtacaatt cgccctcccc gttgtttcaa   600
gaacagatgg agctgttgga agagaaaccc aatccgacca ttctagtcaa cacgttcgat   660
gcactagagc cggaagcctt aaaagcaatt gacaagtaca acttgattgg agttgggcca   720
ttgattccgt ccgctttctt ggacggcaag gatccatcgg acaagtcatt tggaggcgat   780
cttttccaaa aatcaaagga ctcttcatac ctcgagtggc tgaactcgaa gccagaaggg   840
tcggtgattt atgtgtcctt cggaagcatt tctgtgttgg gaaaggccca aatggaggaa   900
atcgcaaaag ggttgttgga ttgcggcctt ccgttcttgt gggttattag agataaggtc   960
ggcaagaagg gagacgataa cgaggcgaag aaagaagaag agatgttgag gtgcagagag  1020
gaattggaag agctcgggat gatagtgccg tggtgtagtc aagtggaggt tctctctagt  1080
ccttcgttgg gttgctttgt gacacattgt gggtggaatt caagtttgga gagcttggtt  1140 tcagggtgc ccgtggtggc gtttcctcag tggacggacc aagggacgaa tgccaagttg  1200
atagaggact attggaagac aggagtgagg gtgacaccaa atgaggaggg gatagttacg  1260
ggtgaggagc tcaagaggtg cttggatttg gtattgggaa gtgggagat tggtgaagac  1320 gtgagaagga atgctaagaa atggaaagat ttggcaagag aggctgtgag tgaaggggac  1380
tcttcggaca agaatctcag ggctttcttg gatcagatca aggttttaaa agatgctagg  1440
cactag                                                            1446

<210> SEQ ID NO 8
<211> LENGTH: 481
<212> TYPE: PRT
<213> ORGANISM: Malus domestica

<400> SEQUENCE: 8

```
Met Val Gln His Arg Phe Leu Leu Val Thr Phe Pro Ala Gln Gly His
1               5                   10                  15

Ile Asn Pro Ser Leu Gln Phe Ala Lys Arg Leu Ile Asn Thr Thr Gly
            20                  25                  30

Ala His Val Thr Tyr Val Thr Ser Leu Ser Ala His Arg Arg Ile Gly
        35                  40                  45

Asn Gly Ser Ile Pro Asp Gly Leu Thr Tyr Ala Pro Phe Ser Asp Gly
    50                  55                  60

Tyr Asp Asp Gly Phe Lys Pro Gly Asp Asn Val Asp Asp Tyr Met Ser
65                  70                  75                  80

Glu Leu Arg Arg Arg Gly Val Gln Ala Ile Thr Asp Leu Val Val Ala
                85                  90                  95

Ser Ala Asn Glu Gly His Pro Tyr Thr Cys Leu Val Tyr Ser Leu Leu
            100                 105                 110

Leu Pro Trp Ser Ala Gly Met Ala His Glu Leu His Leu Pro Ser Val
        115                 120                 125

Leu Leu Trp Ile Gln Pro Ala Thr Val Phe Asp Ile Tyr Tyr Tyr Tyr
    130                 135                 140

Phe Asn Gly Tyr Lys Asp Leu Ile Arg Asp Asn Thr Ser Ser Gly Thr
145                 150                 155                 160

Asn Asn Val Leu Pro Cys Ser Ile Glu Leu Pro Gly Leu Pro Leu Ser
            165                 170                 175

Phe Thr Ser Arg Asp Leu Pro Ser Phe Met Val Asp Thr Asn Pro Tyr
        180                 185                 190

Asn Phe Ala Leu Pro Leu Phe Gln Glu Gln Met Glu Leu Leu Glu Arg
    195                 200                 205

Glu Thr Asn Pro Thr Ile Leu Val Asn Thr Phe Asp Ala Leu Glu Pro
210                 215                 220

Glu Ala Leu Lys Ala Ile Asp Lys Tyr Asn Leu Ile Gly Val Gly Pro
225                 230                 235                 240

Leu Ile Pro Ser Ala Phe Leu Asp Gly Lys Asp Pro Ser Asp Lys Ser
            245                 250                 255

Phe Gly Gly Asp Leu Phe Gln Lys Ser Lys Asp Ser Ser Tyr Leu Glu
        260                 265                 270

Trp Leu Asn Ser Lys Pro Glu Gly Ser Val Ile Tyr Val Ser Phe Gly
    275                 280                 285

Ser Ile Ser Val Leu Gly Lys Ala Gln Met Glu Glu Ile Ala Lys Gly
290                 295                 300

Leu Leu Asp Cys Gly Leu Pro Phe Leu Trp Val Ile Arg Asp Lys Val
305                 310                 315                 320

Gly Lys Lys Gly Asp Asp Asn Glu Ala Lys Lys Glu Glu Met Leu
            325                 330                 335

Arg Cys Arg Glu Glu Leu Glu Glu Leu Gly Met Ile Val Pro Trp Cys
        340                 345                 350

Ser Gln Val Glu Val Leu Ser Ser Pro Ser Leu Gly Cys Phe Val Thr
    355                 360                 365

His Cys Gly Trp Asn Ser Ser Leu Glu Ser Leu Val Ser Gly Val Pro
370                 375                 380

Val Val Ala Phe Pro Gln Trp Thr Asp Gln Gly Thr Asn Ala Lys Leu
385                 390                 395                 400

Ile Glu Asp Tyr Trp Lys Thr Gly Val Arg Val Thr Pro Asn Glu Glu
            405                 410                 415

Gly Ile Val Thr Gly Glu Glu Leu Lys Arg Cys Leu Asp Leu Val Leu
```

```
                420             425             430
Gly Ser Gly Glu Ile Gly Glu Asp Val Arg Arg Asn Ala Lys Lys Trp
        435                 440                 445

Lys Asp Leu Ala Arg Glu Ala Val Ser Glu Gly Asp Ser Ser Asp Lys
    450                 455                 460

Asn Leu Arg Ala Phe Leu Asp Gln Ile Lys Val Leu Lys Asp Ala Arg
465                 470                 475                 480

His

<210> SEQ ID NO 9
<211> LENGTH: 396
<212> TYPE: PRT
<213> ORGANISM: Bacillus licheniformis

<400> SEQUENCE: 9

Met Gly His Lys His Ile Ala Ile Phe Asn Ile Pro Ala His Gly His
1               5                   10                  15

Ile Asn Pro Thr Leu Ala Leu Thr Ala Ser Leu Val Lys Arg Gly Tyr
            20                  25                  30

Arg Val Thr Tyr Pro Val Thr Asp Glu Phe Val Lys Ala Val Glu Glu
        35                  40                  45

Thr Gly Ala Glu Pro Leu Asn Tyr Arg Ser Thr Leu Asn Ile Asp Pro
    50                  55                  60

Gln Gln Ile Arg Glu Leu Met Lys Asn Lys Lys Asp Met Ser Gln Ala
65                  70                  75                  80

Pro Leu Met Phe Ile Lys Glu Met Glu Glu Val Leu Pro Gln Leu Glu
                85                  90                  95

Ala Leu Tyr Glu Asn Asp Lys Pro Asp Leu Ile Leu Phe Asp Phe Met
            100                 105                 110

Ala Met Ala Gly Lys Leu Leu Ala Glu Lys Phe Gly Ile Glu Ala Val
        115                 120                 125

Arg Leu Cys Ser Thr Tyr Ala Gln Asn Glu His Phe Thr Phe Arg Ser
    130                 135                 140

Ile Ser Glu Glu Phe Lys Ile Glu Leu Thr Pro Glu Gln Glu Asp Ala
145                 150                 155                 160

Leu Lys Asn Ser Asn Leu Pro Ser Phe Asn Phe Glu Asp Met Phe Glu
                165                 170                 175

Pro Ala Lys Leu Asn Ile Val Phe Met Pro Arg Ala Phe Gln Pro Tyr
            180                 185                 190

Gly Glu Thr Phe Asp Glu Arg Phe Ser Phe Val Gly Pro Ser Leu Ala
        195                 200                 205

Lys Arg Lys Phe Gln Glu Lys Glu Thr Pro Ile Ile Ser Asp Ser Gly
    210                 215                 220

Arg Pro Val Met Leu Ile Ser Leu Gly Thr Ala Phe Asn Ala Trp Pro
225                 230                 235                 240

Glu Phe Tyr His Met Cys Ile Glu Ala Phe Arg Asp Thr Lys Trp Gln
                245                 250                 255

Val Ile Met Ala Val Gly Thr Thr Ile Asp Pro Glu Ser Phe Asp Asp
            260                 265                 270

Ile Pro Glu Asn Phe Ser Ile His Gln Arg Val Pro Gln Leu Glu Ile
        275                 280                 285

Leu Lys Lys Ala Glu Leu Phe Ile Thr His Gly Gly Met Asn Ser Thr
    290                 295                 300

Met Glu Gly Leu Asn Ala Gly Val Pro Leu Val Ala Val Pro Gln Met
```

```
                305                 310                 315                 320
Pro Glu Gln Glu Ile Thr Ala Arg Arg Val Glu Glu Leu Gly Leu Gly
                    325                 330                 335
Lys His Leu Gln Pro Glu Asp Thr Thr Ala Ala Ser Leu Arg Glu Ala
                    340                 345                 350
Val Ser Gln Thr Asp Gly Asp Pro His Val Leu Lys Arg Ile Gln Asp
                    355                 360                 365
Met Gln Lys His Ile Lys Gln Ala Gly Gly Ala Glu Lys Ala Ala Asp
                    370                 375                 380
Glu Ile Glu Ala Phe Leu Ala Pro Ala Gly Val Lys
385                 390                 395

<210> SEQ ID NO 10
<211> LENGTH: 1763
<212> TYPE: DNA
<213> ORGANISM: Malus domestica

<400> SEQUENCE: 10
```

| | | | | | |
|---|---|---|---|---|---|
| accttgaatg | tatactccca | caagaatttc | aactgcactc | agcttataag | cccacagtac | 60 |
| caaatttttc | aacaatcaac | tacataccta | cttattctac | ttccaacaac | tccacactcc | 120 |
| accgcgcacc | tccggcaatc | gcatacgccg | ccatggtgca | acaccgcttt | ctactcgtca | 180 |
| catttccagc | tcaaggccac | atcaacccct | ccctccaatt | cgccaagcgc | cttatcaaca | 240 |
| ctacaggtgc | gcatgtcacc | tacgttacta | gtctgtcagc | ccatcgccgt | ataggcaatg | 300 |
| gctcaattcc | agatggattg | acctatcgcg | ccttctctga | tgggtacgac | gatgggttta | 360 |
| agcccggcga | caacatcgac | gactacatgt | cagagctgcg | gcgccgcgga | gtacaagcca | 420 |
| ttaccgacct | tgtagtcgca | agtgcaaacg | agggtcaccc | ttacacttgc | ctagtctact | 480 |
| cattacttct | cccttggtcg | gcagggatgg | cacatgaact | tcacctccca | agcgtgctgc | 540 |
| tttggattca | gccagccacg | gttttcgaca | tctactacta | ttactttaac | gggtacaaag | 600 |
| atctcatccg | ggataatact | agttctggta | cgaacaatgt | ccttccatgt | tcaatagaat | 660 |
| taccaggttt | gccattatct | ttcacaagcc | gagaccttcc | ctccttcatg | gtggatacaa | 720 |
| atccgtacaa | tttcgccctc | ccgttgtttc | aagaacagat | ggagctgttg | aaagagaaa | 780 |
| ccaatccgac | cattctagtc | aacacgttcg | atgcactaga | gccggaagcc | ttaaaagcaa | 840 |
| ttgacaagta | caacttgatt | ggagttgggc | cattgattcc | gtccgctttc | ttggacggca | 900 |
| aggatccatc | ggacaagtca | tttggaggcg | atcttttcca | aaaatcaaag | gactcttcat | 960 |
| acctcgagtg | gctgaactcg | aagccagaag | ggtcggtgat | ttatgtgtcc | ttcggaagca | 1020 |
| tttctgtgtt | gggaaaggcc | caaatggagg | aaatcgcaaa | agggttgttg | gattgcggcc | 1080 |
| ttccgttctt | gtgggttatt | agagataagg | tcgacaagaa | gggagacgat | aacgaggcga | 1140 |
| agaaagaaga | agagatgttg | aggtgcagag | aggaattgga | agagctcggg | atgatagtgc | 1200 |
| cgtggtgtag | tcaagtggag | gttctctcta | gtccttcgtt | gggttgcttt | gtgacacatt | 1260 |
| gtgggtggaa | ttcaagtttg | gagagcttgg | tttcaggggt | gcccgtggtg | gcgtttcctc | 1320 |
| agtggacgga | ccaagggacg | aatgccaagt | tgatagagga | ctattggaag | acaggagtga | 1380 |
| gggtgacacc | aaatgaggag | gggatagtta | cgggtgagga | gctcaagagg | tgcttggatt | 1440 |
| tggtattggg | aagtggggag | attggtgaag | acgtgagaag | gaatgctaag | aaatggaaag | 1500 |
| atttggcaag | agaggctgtg | agtgaagggg | actcttcgga | caagaatctc | aaggctttct | 1560 |
| tggatcagat | caaggtttta | aaagatgcta | ggcactagtc | gggtggcggc | ctaggacctg | 1620 |

```
gggcctggca actacgcggc taggtgtcta ggcaggcgcc tagacggatt cgattaaatc    1680
tattatattt cgtgtaagta agtgtatgtt tatgcttaaa atatatatga tgtcatcata    1740
aacaacaaaa tagaatgaca tat                                           1763

<210> SEQ ID NO 11
<211> LENGTH: 1452
<212> TYPE: DNA
<213> ORGANISM: Malus domestica

<400> SEQUENCE: 11
atggcagcgc cgctgcccat cgaaatcgaa ccatcatcaa ctaatggtca accccatctc      60
gccgacgcct acaaccgtca cgtggctgtc gtagccttcc ctttcactag ccatgcaagc     120
gccttgcttg agaccgtgcg ccgcctagcc accgcccttc caaacactct cttctcgttc     180
ttcagcactt caaaatccaa cagctctctc ttttccaaca acagcattga taacatgccg     240
cgtaacataa gggtgtacga tgtggctgac ggggtgccgg aggggtacgt tttcgtgggc     300
aagccgcagg aggacataga gctcttcatg aatgccgcac cggaaaacat ccggaggagc     360
ttagacgctt ccgtggcgga catcgggaag cagatcagct gcttgatcac cgacgccttc     420
cttttggttg gagtccactt ggctgacgag ttggagtgc cttgggtcac tttctggatc     480
tccggactca aatccctctc cgttcatgtg catactgatc tcatccgcga cactattgga     540
actcaaggca ttacaggtcg tgaaaacgac ctcatcgtcg acaaaaatgt taacatccaa     600
ggtctctcca atgtacgaat caaagactta gcggaaggag tcattttcgg aaacttggac     660
tcggtaattt ccggcatgct acttcagatg ggacggctcc tccccgtgc caccgcagtt      720 ttcatgaacg gcttcgaaga attggaactc cccataccaa acgacctaaa gtccaaagtc     780
aacaaactcc tcaacgtagg accttccaac gtagcatccc cgctgccacc gctgccgcca     840
tcagatgctt gcttgtcatg gctagacaag caacaggctc catcctccgt cgtgtacata     900
agcttcggga cagtggcgag cccagcggag aaggagcaga tggcaatagc ggaggccctg     960
gaagccaccg gagcacccct cttgtggtct atcaaggaca gctgcaagac accgttgctg    1020
aacgagttct tgacaaaaac attgtcaaag ctgaacggga tggtggtgcc gtgggctcca    1080
cagccgcatg tactggccca cgattcggtc ggagccttcg tgtcgcattg cggctggaac    1140
tcgataatgg agactatagc aggacgggtg cccatgattt gtaggccata ttttgcagac    1200
cagaggctta atgcaaggat ggtggaggag gtgtttgaga tcggggtaac cgtggaggat    1260
ggagttttta ccagggaggg gctggtaaaa agcttggaag tggttttgtc gcctgaaagt    1320
gggaggaaat tcagagacaa tataaagagg gtcaaacaac tggcagtaga ggcggttgga    1380
ccacaaggga gctccactcg gaacttcaaa tcgctgttgg acatcgtatc aggatccaat    1440
tatcaagtat ag                                                       1452

<210> SEQ ID NO 12
<211> LENGTH: 483
<212> TYPE: PRT
<213> ORGANISM: Malus domestica

<400> SEQUENCE: 12

Met Ala Ala Pro Leu Pro Ile Glu Ile Glu Pro Ser Ser Thr Asn Gly
1               5                   10                  15

Gln Pro His Leu Ala Asp Ala Tyr Asn Arg His Val Ala Val Val Ala
            20                  25                  30

Phe Pro Phe Thr Ser His Ala Ser Ala Leu Leu Glu Thr Val Arg Arg
```

```
                    35                  40                  45
Leu Ala Thr Ala Leu Pro Asn Thr Leu Phe Ser Phe Phe Ser Thr Ser
 50                  55                  60
Lys Ser Asn Ser Ser Leu Phe Ser Asn Asn Ser Ile Asp Asn Met Pro
 65                  70                  75                  80
Arg Asn Ile Arg Val Tyr Asp Val Ala Asp Gly Val Pro Glu Gly Tyr
                    85                  90                  95
Val Phe Val Gly Lys Pro Gln Glu Asp Ile Glu Leu Phe Met Asn Ala
                   100                 105                 110
Ala Pro Glu Asn Ile Arg Arg Ser Leu Asp Ala Ser Val Ala Asp Ile
                   115                 120                 125
Gly Lys Gln Ile Ser Cys Leu Ile Thr Asp Ala Phe Leu Trp Phe Gly
                   130                 135                 140
Val His Leu Ala Asp Glu Leu Gly Val Pro Trp Val Thr Phe Trp Ile
145                 150                 155                 160
Ser Gly Leu Lys Ser Leu Ser Val His Val His Thr Asp Leu Ile Arg
                   165                 170                 175
Asp Thr Ile Gly Thr Gln Gly Ile Thr Gly Arg Glu Asn Asp Leu Ile
                   180                 185                 190
Val Asp Lys Asn Val Asn Ile Gln Gly Leu Ser Asn Val Arg Ile Lys
                   195                 200                 205
Asp Leu Ala Glu Gly Val Ile Phe Gly Asn Leu Asp Ser Val Ile Ser
                   210                 215                 220
Gly Met Leu Leu Gln Met Gly Arg Leu Leu Pro Arg Ala Thr Ala Val
225                 230                 235                 240
Phe Met Asn Gly Phe Glu Glu Leu Glu Leu Pro Ile Pro Asn Asp Leu
                   245                 250                 255
Lys Ser Lys Val Asn Lys Leu Leu Asn Val Gly Pro Ser Asn Val Ala
                   260                 265                 270
Ser Pro Leu Pro Pro Leu Pro Pro Ser Asp Ala Cys Leu Ser Trp Leu
                   275                 280                 285
Asp Lys Gln Gln Ala Pro Ser Ser Val Val Tyr Ile Ser Phe Gly Thr
                   290                 295                 300
Val Ala Ser Pro Ala Glu Lys Glu Gln Met Ala Ile Ala Glu Ala Leu
305                 310                 315                 320
Glu Ala Thr Gly Ala Pro Phe Leu Trp Ser Ile Lys Asp Ser Cys Lys
                   325                 330                 335
Thr Pro Leu Leu Asn Glu Phe Leu Thr Lys Thr Leu Ser Lys Leu Asn
                   340                 345                 350
Gly Met Val Val Pro Trp Ala Pro Gln Pro His Val Leu Ala His Asp
                   355                 360                 365
Ser Val Gly Ala Phe Val Ser His Cys Gly Trp Asn Ser Ile Met Glu
                   370                 375                 380
Thr Ile Ala Gly Arg Val Pro Met Ile Cys Arg Pro Tyr Phe Ala Asp
385                 390                 395                 400
Gln Arg Leu Asn Ala Arg Met Val Glu Glu Val Phe Glu Ile Gly Val
                   405                 410                 415
Thr Val Glu Asp Gly Val Phe Thr Arg Glu Gly Leu Val Lys Ser Leu
                   420                 425                 430
Glu Val Val Leu Ser Pro Glu Ser Gly Arg Lys Phe Arg Asp Asn Ile
                   435                 440                 445
Lys Arg Val Lys Gln Leu Ala Val Glu Ala Val Gly Pro Gln Gly Ser
                   450                 455                 460
```

```
-continued

Ser Thr Arg Asn Phe Lys Ser Leu Leu Asp Ile Val Ser Gly Ser Asn
465                 470                 475                 480

Tyr Gln Val
```

IDENTIFICATION AND CHARACTERIZATION OF UDP-GLUCOSE:PHLORETIN 4'-O-GLUCOSYL TRANSFERASE FROM *MALUS X DOMESTICA* BORKH

RELATED APPLICATIONS

This application is a National Phase of PCT Patent Application No. PCT/IL2017/050310 having International filing date of Mar. 9, 2017, which claims the benefit of priority under 35 USC § 119(e) of U.S. Provisional Patent Application No. 62/305,591, filed on Mar. 9, 2016. The contents of the above applications are all incorporated by reference as if fully set forth herein in their entirety.

SEQUENCE LISTING STATEMENT

The ASCII file, entitled 75326SequenceListing.txt, created on Sep. 6, 2018 comprising 19,949 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a 4'-O-glycosyltransferase and, more particularly, but not exclusively, to the use of same for producing trilobatin and for engineering cells and plants with increased trilobatin content.

Apple (*Malus×domestica* Borkh.) is an agriculturally and economically important source of food and beverage. Apples accumulate high levels of diverse phenolic antioxidants, including flavonoids and biphenyl phytoalexins, the level of which may depend on many factors, such as genotype, developmental stage, or biotic stress.

Among common phenylpropanoid derivatives, apples are characterized by the presence of dihydrochalcones (DHCs), structures closely related to common flavonoid precursors, the chalcones. Like other flavonoids, DHCs exhibit a wide diversity of hydroxyl and glucosyl substitution patterns. 3-OH-phloretin, phloridzin (phloretin-2'-O-glucoside) (illustrated by no. 7 in FIG. 4), trilobatin (phloretin-4'-O-glucoside) (illustrated by no. 6 in FIGS. 1 and 4) and sieboldin (3-hydroxyphloretin-4'-O-glucoside) accumulate in different combinations in the stems, leaves, flowers and fruits of apple plants.

The physiological function of the DHCs planta remains unresolved. They have been suggested to act as UV filters in leaves or to play a role as potent antioxidants and in resistance to pathogens, but conclusive evidence is still missing. For instance, phloretin (illustrated by no. 5 in FIGS. 1 and 4), a simple dihydrochalcone found in the plant kingdom, has inhibitory activity against the glucose co-transporter 1 and a proven antioxidant activity. DHCs have been reported to display anti-carcinogenic activity, inhibit cardiovascular diseases or to be a potential drug for Alzheimer's disease. Despite their high potential as drugs and food additives the use of DHCs is still limited due to water insolubility and low bioavailability, which in part can be improved by glycosylation.

Glucosylation at the 4'-position of phloretin (illustrated by no. 5 in FIGS. 1 and 4) generates a sweet tasting compound, trilobatin (illustrated by no. 6 in FIGS. 1 and 4), also known as pruning dihydrochalcone. Trilobatin has been previously detected in the leaves of *Vitis* species, in *Lithocarpus polystachyus*, and is also present in different *Malus* species including *M. domestica* and *M. trilobata*. Other dihydrochalcone derivatives are sweet tasting as well; neohesperidin dihydrochalcone (NHDC) and naringin dihydrochalcone, the latter found to accumulate in *Oxytropis myriophylla*, are up to 1000 fold sweeter than sucrose per weight unit, and are stable under heat and a wide pH range. Dihydrochalcones have also been documented to function as bitterness blockers and flavor enhancers with diverse use in the food, beverage and pharmaceutical industries. Altogether, about 200 different dihydrochalcones are known from 30 plant families, including *Camellia japonica*, *Fragaria×ananassa*, *Lithocarpus polystachyus*, legumes and *Citrus* species.

The biosynthetic pathway leading to trilobatin in planta has not been fully resolved as yet. The condensation of one molecule of 4-dihydrocoumaroyl-CoA (illustrated by no. 3 in FIG. 1) and three molecules of malonyl-CoA is catalyzed by chalcone synthase to yield phloretin (as illustrated in FIG. 1).

The attachment of a glucose moiety to phloretin at the 4' position is suggested to be the final step in the formation of trilobatin. Ono et al. [Ono E. et al., *P. Natl. Acad. Sci. USA* (2006) 103: 11075-11080] have shown that glycosylation of chalcones can be catalyzed by a recombinant chalcone 4'-O-glucosyltransferase isolated from snapdragon (*Antirrhinum majus*). Recently, a functionally expressed UDP-glucosyltransferase (UGT) from a bacteria, *Bacillus lichentfomis*, has been shown to catalyze the conversion of phloretin to trilobatin [Pandey R. P. et al., *Appl. Environ. Microb.* (2013) 79, 3516-3521].

U.S. Patent Application No. 20110030098 discloses a method for producing a plant cell or plant with increased phlorizin or phloretin glycosyltransferase activity by transformation of the plant cell or plant with a polynucleotide encoding a polypeptide with phloretin glycosyltransferase activity. U.S. 20110030098 also provides host cells, plant cells and plants, genetically modified to contain and or express the polynucleotides.

SUMMARY OF THE INVENTION

According to an aspect of some embodiments of the present invention there is provided a method of producing trilobatin, the method comprising contacting a polypeptide comprising an amino acid sequence at least 90% identical to SEQ ID NO: 8 and having a 4'-O-glycosyltransferase activity with phloretin and UDP-glucose under conditions which allow the formation of trilobatin, thereby producing trilobatin.

According to an aspect of some embodiments of the present invention there is provided a method of producing a plant which produces trilobatin, the method comprising upregulating in the plant expression of a polypeptide comprising an amino acid sequence at least 90% identical to SEQ ID NO: 8 and having a 4'-O-glycosyltransferase activity, and wherein the plant comprises phloretin and UDP-glucose, thereby producing the plant.

According to an aspect of some embodiments of the present invention there is provided a transgenic plant or plant cell comprising an exogenous nucleic acid sequence encoding a polypeptide comprising an amino acid sequence at least 90% identical to SEQ ID NO: 8 and having a 4'-O-glycosyltransferase activity.

According to an aspect of some embodiments of the present invention there is provided a method of producing a transgenic plant the method comprising introducing into cells of the plant a nucleic acid construct comprising a nucleic acid sequence encoding a polypeptide comprising an amino acid sequence at least 90% identical to SEQ ID NO: 8 and having a 4'-O-glycosyltransferase activity.

According to an aspect of some embodiments of the present invention there is provided a cell lysate of the cell of some embodiments of the invention.

According to an aspect of some embodiments of the present invention there is provided a composition comprising trilobatin of the cell lysate of some embodiments of the invention.

According to an aspect of some embodiments of the present invention there is provided a composition comprising trilobatin generated according to the method of some embodiments of the invention.

According to some embodiments of the invention, the method being effected in vivo.

According to some embodiments of the invention, in vivo is in a plant cell.

According to some embodiments of the invention, in vivo is in a microorganism.

According to some embodiments of the invention, the microorganism is selected from the group of yeast and bacteria.

According to some embodiments of the invention, the method being effected in vitro.

According to some embodiments of the invention, in vitro is a cell free system.

According to some embodiments of the invention, the method further comprises purifying the trilobatin.

According to some embodiments of the invention, the upregulating comprises genetic engineering.

According to some embodiments of the invention, the upregulating comprises crossing with a plant which expresses the polypeptide comprising an amino acid sequence at least 90% identical to SEQ ID NO: 8.

According to some embodiments of the invention, the plant cells comprise a substrate selected from the group consisting of phloretin, trilobatin, phloridzin, quercetin, naringenin and butein.

According to some embodiments of the invention, the plant cell comprises a UDP-glucose substrate.

According to some embodiments of the invention, the plant cell comprises a phloretin substrate and a UDP-glucose substrate.

According to some embodiments of the invention, when the transgenic plant or plant cell comprises phloretin and UDP-glucose, the transgenic plant or plant cell produces trilobatin.

According to some embodiments of the invention, the method or transgenic plant or plant cell further comprises selecting the cell or plant expressing the polypeptide product of the SEQ ID NO: 8 or at least 90% identical to the SEQ ID NO: 8.

According to some embodiments of the invention, the method or transgenic plant or plant cell further comprises selecting the cell or plant comprising a 4'-O-glycosyltransferase activity.

According to some embodiments of the invention, the method or transgenic plant or plant cell, further comprises selecting the cell or plant producing the trilobatin.

According to some embodiments of the invention, the plant cell is selected from the group consisting of a cell of a leaf, a cell of a flower, a cell of a fruit.

According to some embodiments of the invention, the plant is of the *Malus* family.

According to some embodiments of the invention, the plant is selected from the group consisting of a *Malus domestica, Malus trilobata, Malus sieboldii, Vitis piasezkii maxim, Vitis saccharifera makino, Lithocarpus polystachyus, Symplocos paniculata, Smilax glyciphylla* and *Fragaria*.

According to some embodiments of the invention, the cell lysate comprises trilobatin.

According to some embodiments of the invention, the composition being a food, feed or beverage product.

According to some embodiments of the invention, the composition being in a form selected from the group consisting of a granulated form, a powder form, a paste form and a liquid form.

According to some embodiments of the invention, the composition is selected from the group consisting of a jelly, a sauce, a syrup, a relish, a wine, a cereal, a flake, a bar, a snack, a spread, a paste, a dip, a flour, a porridge, a beverage, an infusion, a decoction, a tincture, an extract, and a juice.

According to some embodiments of the invention, the composition is selected from the group consisting of a dried fruit, a fresh fruit, a frozen fruit, a baked fruit, a boiled fruit, a steamed fruit, a stir-dried fruit and a grilled fruit.

According to some embodiments of the invention, the composition being formulated as a pharmaceutical composition.

According to some embodiments of the invention, the pharmaceutical composition is for use for the treatment of a carcinogenic disease.

According to some embodiments of the invention, the pharmaceutical composition is for use for the treatment of a cardiovascular disease.

According to some embodiments of the invention, the pharmaceutical composition is for use for the treatment of diabetes.

According to some embodiments of the invention, the pharmaceutical composition is for use for the treatment of a neurodegenerative disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
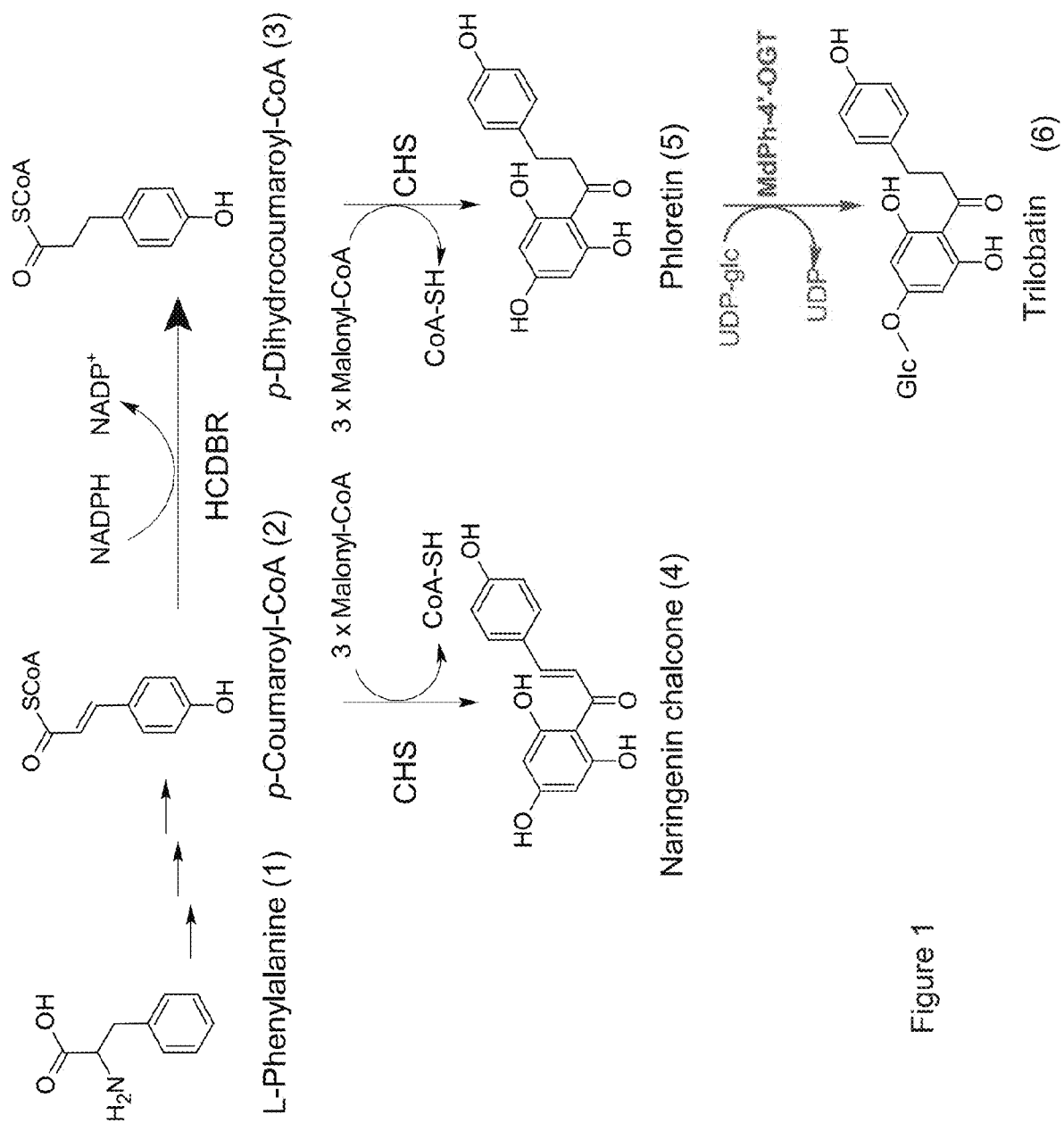

FIG. 1 is a schematic illustration of a proposed biosynthetic pathway leading to dihydrochalcone glycosides in apple, CHS, Chalcone synthase; CHI, Chalcone isomerase; HCDBR, Hydroxycinnamoyl-CoA double bond reductase; MdPh-4'-OGT, Phloretin 4'-O-glucosyltransferase, highlighted by red coloring.

Figure 2:
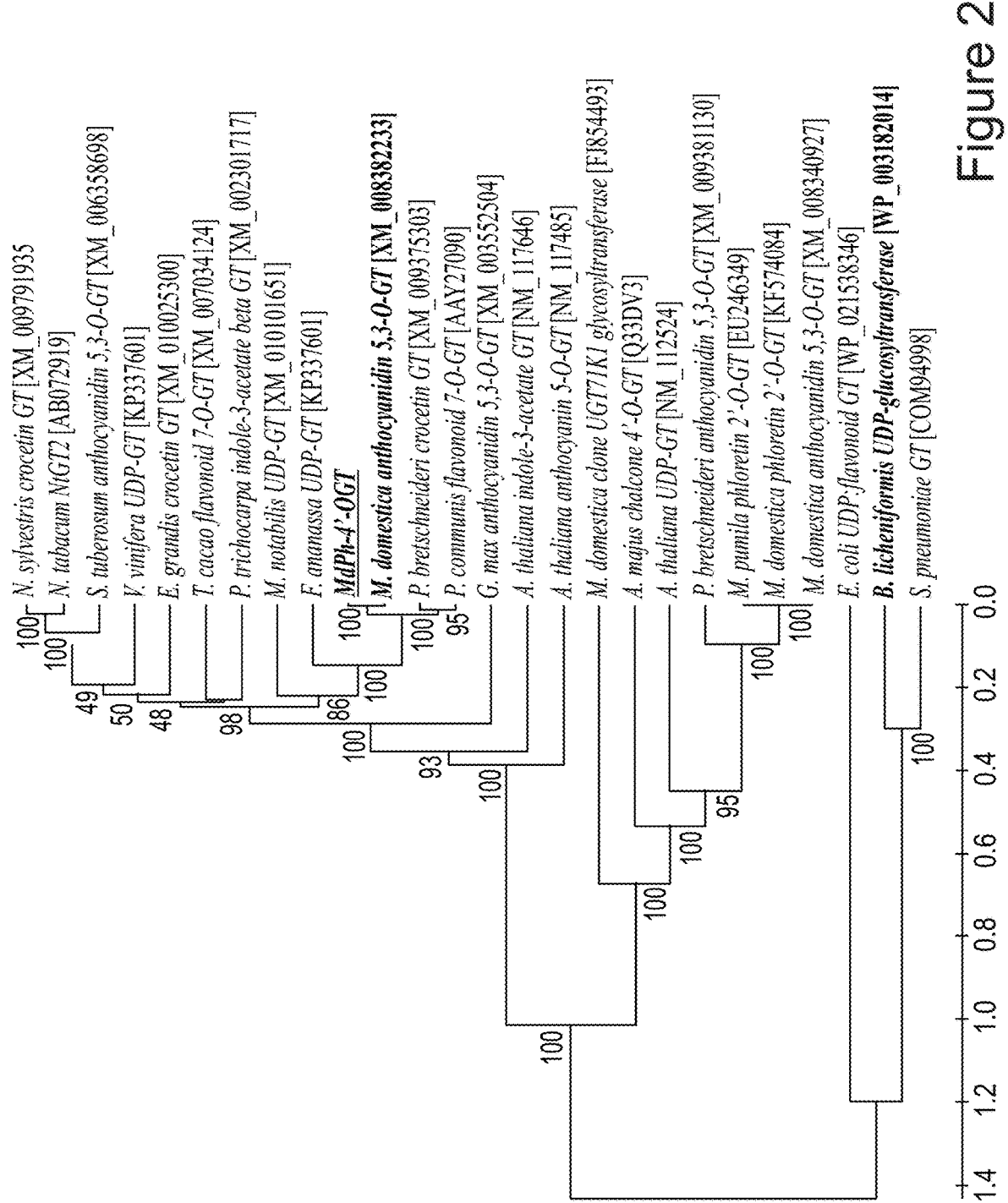

FIG. 2 is a schematic illustration of a neighbor-joining tree of deduced amino acid sequences of plant and some bacterial UDP-glucosyltransferase proteins. The MdPh-protein identified in this study is highlighted by bold underlined text. The bootstrap method was performed with 1000 replicates.

FIGS. 3A-H are graphs illustrating LC-MS analysis of a reaction product of recombinant MdPh-4'-OGT with phloretin (illustrated by no. 5 in FIG. 1) and UDP-glucose. (FIG. 3A) Enzyme activity of the recombinant MdPh-4'-OGT with phloretin as a substrate. (FIG. 3B) Enzyme activity of the boiled recombinant MdPh-4'-OGT with UDP-glucose as a co-substrate. (FIG. 3C) Phloterin standard. (FIG. 3D) Trilobatin (illustrated by no. 6 in FIG. 1) standard. (FIG. 3E) Phloridzin (illustrated by no. 7 in FIG. 4) standard. (FIG. 3F) Mass spectra of phloretin. (FIG. 3G) Mass spectra of trilobatin. (FIG. 3H) Mass spectra of phloridzin. m/z=mass-to-charge. The insert shows the structure of phloretin, trilobatin and phloridzin.

FIG. 4 illustrates the substrate specificity of His-tagged, affinity chromatography-purified recombinant MdPh-4'-OGT. Of note, the activity with phloretin was arbitrarily set at 100%, for reactions containing 500 ng enzymes for 1 hour. Substrates analyzed are indicated. The enzyme assays were carried out in a buffer containing 50 mM Tris-HCl pH 7.5, and 2 mM 2-mercptoethanol, with 50 µM substrates and 2 mM UDP-glucose.

FIGS. 5A-D are graphs illustrating the Phloretin4'-O-glycosyltransferase activity of the recombinant MdPh-4'-OGT protein. The graphs show steady state kinetic measurements of MdPh-4'-OGT using phloretin as the varying co-substrate (FIG. 5A) or UDP-glucose as the varying co-substrate (FIG. 5B). Determination of the pH optimum (FIG. 5C) and temperature optimum (FIG. 5D) of MdPh-4'-OGT activity with phloretin and UDP-glucose substrates.

Figure 6:
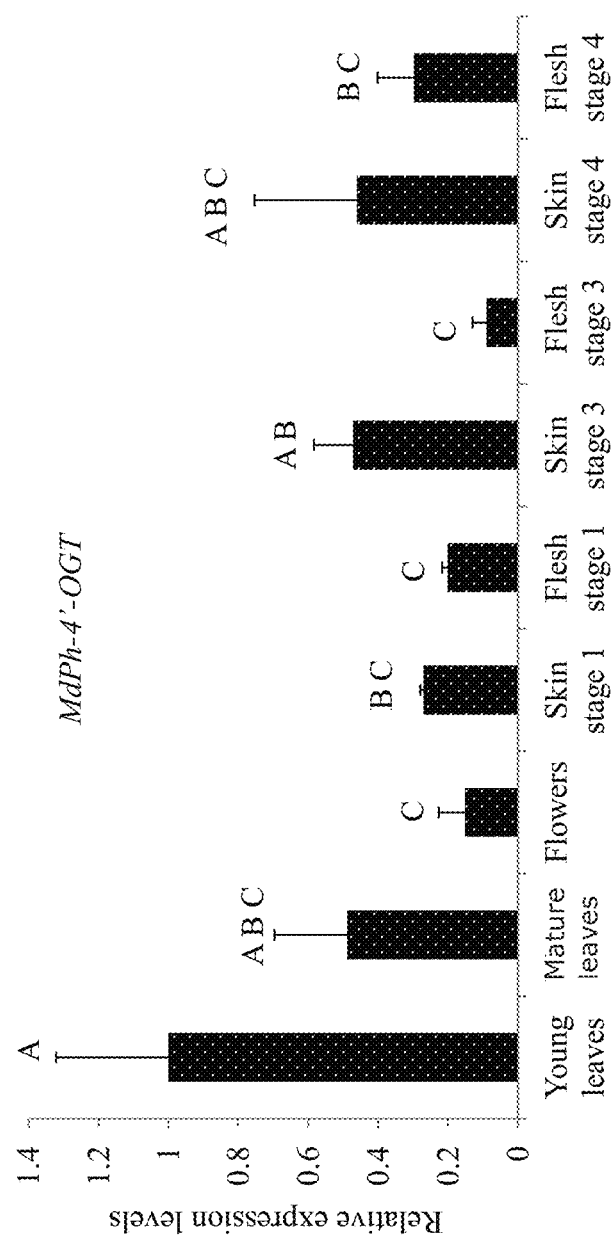

FIG. 6 is a graph illustrating the expression patterns of MdPh-4'-OGT in different apple "Golden delicious" tissues. Quantification of MdPh-4'-OGT transcript levels were measured by real-time qRT-PCR analysis and normalized relative to actin. Bars labeled with different letters indicate the significant differences as determined by JMP statistical software ($P \leq 0.05$; Tukey-Kramer honestly significant difference test). All analyses were performed using three biological replicates.

FIG. 7 illustrates the sequences of open reading frames and encoded proteins of MdPh-4'-OGT (UDP-glucose:flavonoid 7-O-glucosyltransferase). Of note, the nucleic acid sequence of MdPh-4'-OGT is set forth in SEQ ID NO: 7 and the amino acid sequence of MdPh-4'-OGT is set forth in SEQ ID NO: 8.

Figure 8:
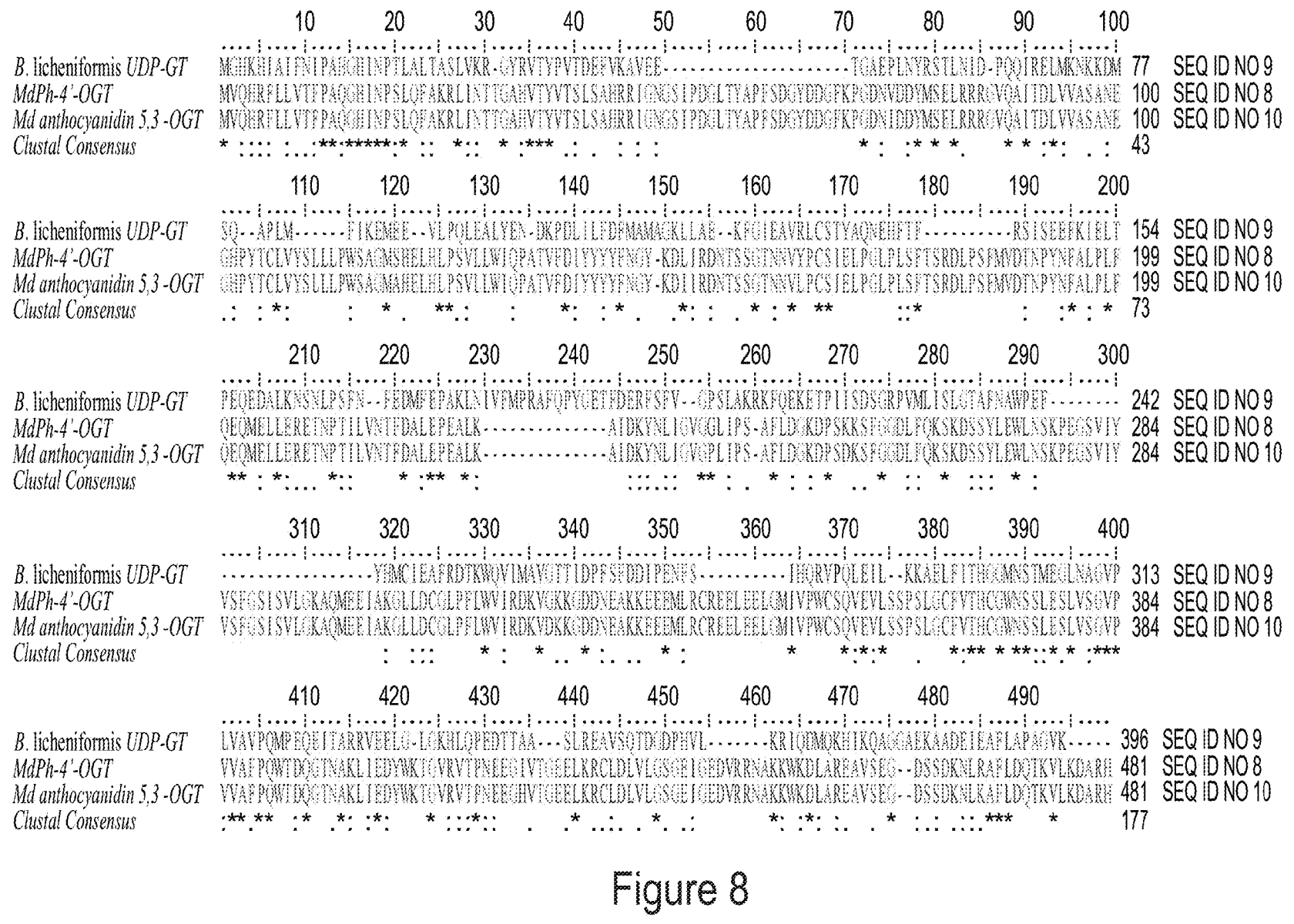

FIG. 8 illustrates a multiple alignment of amino acid sequences from *Malus* MdPh-4'-OGT (UDP glucose: flavonoid 7-O-glucosyltransferase, AAX16493) (set forth in SEQ ID NO: 8), *M. domestica* anthocyanidin 5,3-O-GT (XM_008382233) (set forth in SEQ ID NO: 10), and UDP-glucosyltransferase from *B. licheniformis* (WP_003182014) (set forth in SEQ ID NO: 9) [Pandey R. P. et at, (2013), supra].

Figure 9:
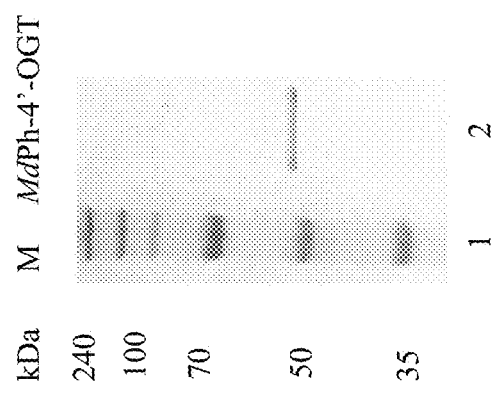
Figure 11A:
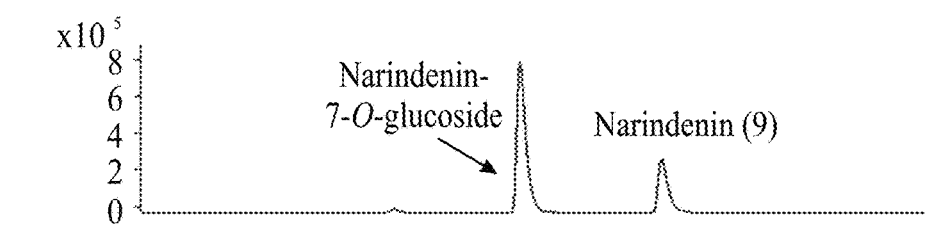
Figure 11B:
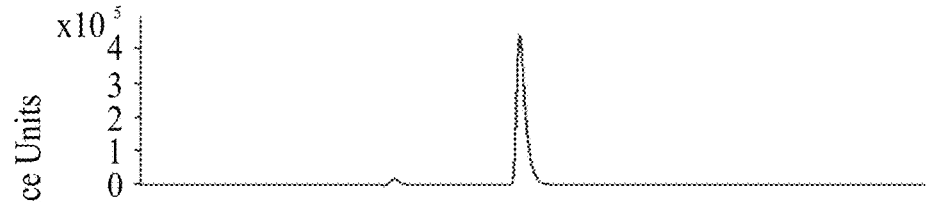
Figure 11C:
Figure 11D:
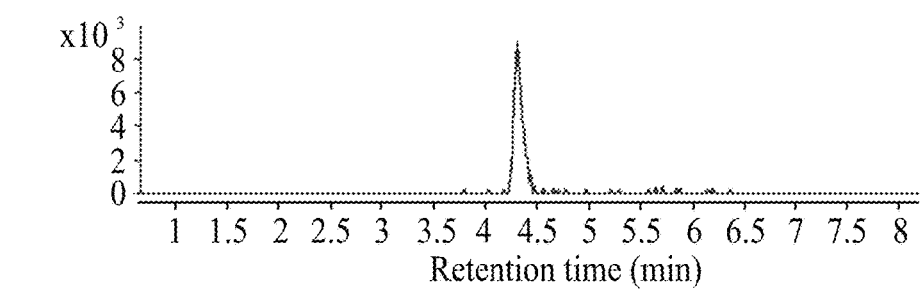
Figure 11E:
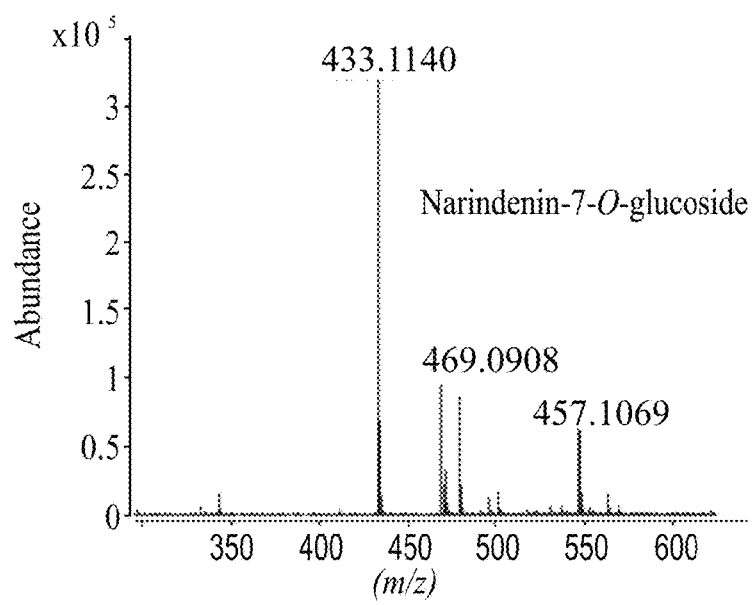

FIG. 9 is a photograph illustrating SDS-PAGE analysis of purified recombinant MdPh-4'-OGT. Lane 1: Molecular mass markers; Lane 2: Soluble extracts from recombinant MdPh-4'-OGT after Ni-NTA matrix chromatography.

FIGS. 10A-F are graphs illustrating LC-MS analysis of reaction products of recombinant MdPh-4'-OGT with trilobatin or phloridzin and UDP-glucose. (FIG. 10A) Enzyme activity of the recombinant MdPh-4'-OGT with phloridzin as a substrate. (FIG. 10B) Enzyme activity of the boiled recombinant MdPh-4'-OGT with phloridzin. (FIG. 10C) Enzyme activity of the recombinant MdPh-4'-OGT with trilobatin as a substrate. (FIG. 10D) Enzyme activity of the boiled recombinant MdPh-4'-OGT with trilobatin. (FIG. 10E) Mass spectra of phloridzin di-O-glucoside. (FIG. 10F) Mass spectra of trilobatin di-O-glucoside. m/z=mass-to-charge. S=substrate; P=product.

FIGS. 11A-E are graphs illustrating LC-MS analysis of reaction product of recombinant MdPh-4'-OGT with naringenin and UDP-glucose. (FIG. 11A) Enzyme activity of the recombinant MdPh-4'-OGT with naringenin as a substrate and UDP-glucose as a co-substrate. (FIG. 11B) Enzyme activity of the boiled recombinant MdPh-4'-OGT with naringenin as a substrate. (FIG. 11C) Naringenin standard. (FIG. 11D) Naringenin-7-O-glucoside standard. (FIG. 11E) Mass spectra of naringenin-7-O-glucoside. m/z=mass-to-charge.

FIGS. 12A-D are graphs illustrating LC-MS analysis of reaction products of recombinant MC/Ph-4'-OGT with quercetin and UDP-glucose. (FIG. 12A) Enzyme activity of the recombinant MdPh-4'-OGT with quercetin as a substrate and UDP-glucose as a co-substrate. (FIG. 12B) Enzyme activity of the boiled recombinant MC/Ph-4'-OGT with quercetin as a substrate. (FIG. 12C) quercetin-7-O-glucoside standard. (FIG. 12D) Mass spectra of quercetin-7-O-glucoside. m/z=mass-to-charge.

DESCRIPTION OF SPECIFIC EMBODIMENTS OF THE INVENTION

The present invention, in some embodiments thereof, relates to a 4'-O-glycosyltransferase and, more particularly, but not exclusively, to the use of same for producing trilobatin and for engineering cells and plants with increased trilobatin content.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Apples (*Malus×domestica* Brokh.) are among the world's most important agricultural and economical important source of food and beverage. Many of the health beneficial properties of apples are suggested to be due to polyphenolic metabolites, including various dihydrochalcones (DHCs). DHCs exhibit a wide diversity of hydroxyl and glucosyl substitution patterns and accumulate in different combinations in the stems, leaves, flowers and fruits of apple plants.

Although many of the genes and enzymes involved in polyphenol biosynthesis are known in many plant species, the specific reactions that lead to the biosynthesis of the sweet tasting dihydrochalcones, such as trilobatin, are unknown.

The present inventor has identified a novel position-specific glycosyltransferase which glycosylates phloretin in the presence of UDP-glucose to form trilobatin. This glycosyltransferase was designated *M. domestica* UDP-glucose:phloretin 4'-O-glycosyltransferase (MdPh-4'-OGT). The gene encoding MdPh-4'-OGT was cloned and characterized from *M. domestica* leaves. MdPh-4'-OGT was further found to be expressed in apple fruit and leaves in accordance with the accumulation of trilobatin in apple tissues. This novel gene can be used to metabolically engineer cells and crop plants to contain trilobatin as a natural sweetener, a nutritional supplement, for improved plant disease resistance and for therapeutics.

Thus, according to one aspect of the present invention there is provided a method of producing trilobatin, the method comprising contacting a polypeptide comprising an amino acid sequence at least 90% identical to SEQ ID NO: 8 and having a 4'-O-glycosyltransferase activity with phloretin and UDP-glucose, thereby producing trilobatin.

The present invention further provides a method of producing a plant which produces trilobatin, the method comprising upregulating in the plant expression of a polypeptide comprising an amino acid sequence at least 90% identical to SEQ ID NO: 8 and having a 4"-O-glycosyltransferase activity, and wherein the plant comprises phloretin and UDP-glucose, thereby producing the plant.

The term "trilobatin" as used herein refers to the dihydrochalcone glycoside also referred to as phloretin-4'-O-glucoside or 1-Propanone, 1-(4-(beta-D-glucopyranosyloxy)-2,6-dihydroxyphenyl)-3-(4-hydroxyphenyl), the structure of which is shown below (Formula I):

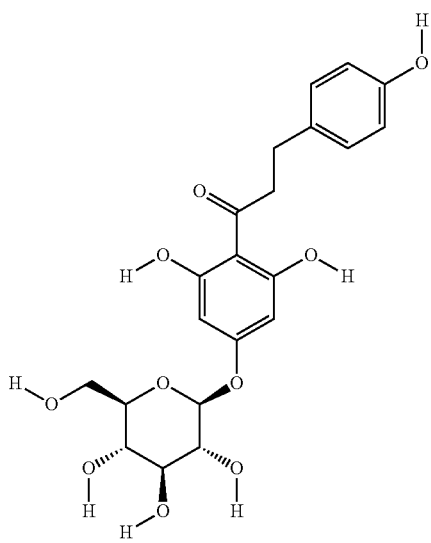 [SMILES: O=C(CCc1ccc(O)cc1)c1c(O)cc(O[C@@H]2O[C@H](CO)[C@@H](O)[C@H](O)[C@H]2O)cc1O]

The term "phloretin" as used herein refers to the dihydrochalcone also referred to as dihydronaringenin, phloretol or 3-(4-hydroxyphenyl)-1-(2,4,6-trihydroxyphenyl)-1-propanone, the structure of which is shown below (Formula II):

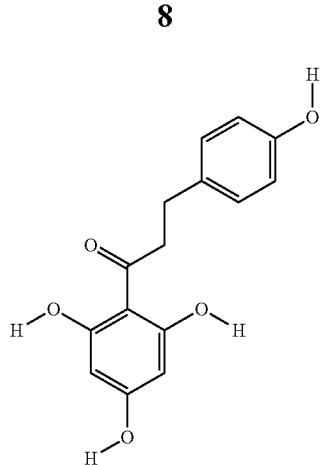

The term "UDP-glucose" as used herein refers to the uridine diphosphate glucose also referred to as uracil-diphosphate glucose, a nucleotide sugar, the structure of which is shown below (Formula III):

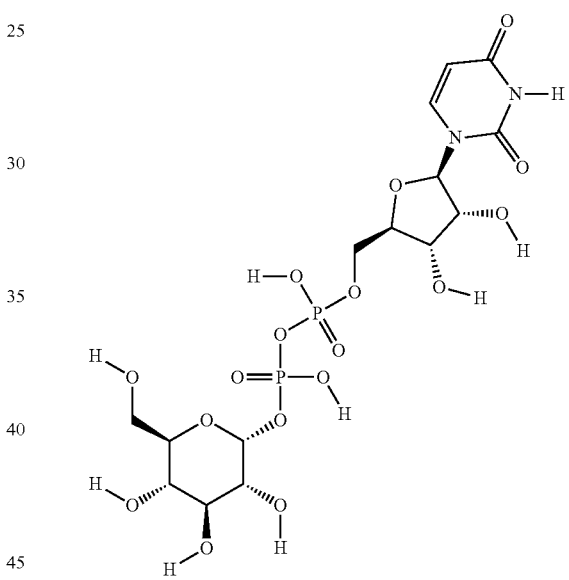

The term "having a 4'-O-glycosyltransferase activity" as used herein refers to the attachment of a glucose moiety to a substrate at the 4-hydroxyl group.

Trilobatin biosynthesis typically requires the co-substrates phloretin and UDP-glucose and involves attachment of a glucose moiety to phloretin at the 4-hydroxyl group. The attachment of a glucose moiety to phloretin at the 4-hydroxyl group is typically achieved by an enzyme having a 4'-O-glycosyltransferase activity. Such a glycosyltransferase enzyme catalyzes the transfer of a saccharide moiety (e.g. glucose) from an activated nucleotide sugar (e.g. UDP-glucose) to the 4-hydroxyl group of the acceptor molecule (e.g. phloretin). The present inventor has uncovered this enzyme as *Malus×domestica* UDP-glucose:phloretin 4'-O-glycosyltransferase (also termed herein MdPh-4'-OGT).

According to one embodiment, the polypeptide catalyzing trilobatin biosynthesis comprises an amino acid sequence at least 90% identical to SEQ ID NO: 8. According to some embodiments, the amino acid sequence is at least 90% homologous to SEQ ID NO: 8.

According to one embodiment, the polypeptide catalyzing trilobatin biosynthesis comprises an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% homology or identity to SEQ ID NO: 8.

According to one embodiment, the polypeptide catalyzing trilobatin biosynthesis comprises an amino acid sequence having at least 90%, at least 91%, at least 92%, at least 93%, at least 94%, at least 95%, at least 96%, at least 97%, at least 98%, at least 99%, or 100% homology or identity to SEQ ID NO: 8.

According to a specific embodiment, the amino acid sequence of the MdPh-4'-OGT polypeptide catalyzing trilobatin biosynthesis is as set forth in SEQ ID NO: 8. In some cases, SEQ ID NO: 8 is also referred to as UDP-glucose:flavonoid 7-O-glucosyltransferase (as set forth in accession number AAX16493).

According to the present invention, homologous sequences include both orthologous and paralogous sequences.

The term "paralogous" relates to gene-duplications within the genome of a species leading to paralogous genes. The term "orthologous" relates to homologous genes in different organisms due to ancestral relationship. Thus, orthologs are evolutionary counterparts derived from a single ancestral gene in the last common ancestor of given two species and therefore have great likelihood of having the same function.

One option to identify orthologues in monocot plant species is by performing a reciprocal BLAST search. This may be done by a first blast involving blasting the sequence-of-interest against any sequence database, such as the publicly available NCBI database which may be found at: ncbi(dot)nlm(dot)nih(dot)gov. If orthologues in rice were sought, the sequence-of-interest would be blasted against, for example, the 28,469 full-length cDNA clones from *Oryza sativa* Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [ebi(dot)ac(dot)uk/Tools/clustalw2/index(dot)html], followed by a neighbor-joining tree (wikipedia(dot)org/wikit-Neighbor-joining) which helps visualizing the clustering.

Homology (e.g., percent homology, sequence identity+ sequence similarity) can be determined using any homology comparison software computing a pair vise sequence alignment.

As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9].

Identity (e.g., percent homology) can be determined using any homology comparison software, including for example, the BlastN software of the National Center of Biotechnology Information (NCBI) such as by using default parameters.

According to some embodiments of the invention, the identity is a global identity, i.e., an identity over the entire amino acid or nucleic acid sequences of the invention and not over portions thereof.

According to some embodiments of the invention, the term "homology" or "homologous" refers to identity of two or more nucleic acid sequences; or identity of two or more amino acid sequences; or the identity of an amino acid sequence to one or more nucleic acid sequence.

According to some embodiments of the invention, the homology is a global homology, i.e., an homology over the entire amino acid or nucleic acid sequences of the invention and not over portions thereof.

The degree of homology or identity between two or more sequences can be determined using various known sequence comparison tools which are described in WO2014/102774.

Local alignments tools, which can be used include, but are not limited to, the tBLASTX algorithm, which compares the six-frame conceptual translation products of a nucleotide query sequence (both strands) against a protein sequence database. Default parameters include: Max target sequences: 100; Expected threshold: 10; Word size: 3; Max matches in a query range: 0; Scoring parameters: Matrix—BLOSUM62; filters and masking: Filter—low complexity regions.

In general, the method of producing a trilobatin may be effected either in vitro or in vivo. It will be appreciated that some steps of the invention may be performed in vitro, whereas others may be performed in vivo. Such a determination is well within the capability of one of skill in the art.

When the methods are performed in vivo, the methods employ use of at least one host cell expressing the enzyme of the invention.

Host cells suitable for producing trilobatin include, for example, microorganisms (e.g. bacterial, fungal, yeast cells), insect cells, mammalian cells and plant cells.

According to a specific embodiment the host cell is a plant cell or a microorganism.

According to one embodiment, the method of producing trilobatin is effected in a. cell exogenously expressing a polypeptide comprising an amino acid sequence at least 90% identical to SEQ ID NO: 8 and having a 4'-O-glycosyltransferase activity.

According to one embodiment, a polypeptide comprising an amino acid sequence at least 90% identical to SEQ ID NO: 8 and having a 4'-O-gycosyltransferase activity may also be endogenously expressed by the cell, in such a case, polypeptide expression is upregulated by at least about 5%, 10%, 20%, 30%, 40%, 50%, 60%, 70%, 80%, 90%, 100%, or more as compared to a cell not expressing the exogenous polypeptide.

According to one embodiment, expression of the polypeptides of the invention comprising an amino acid sequence at least 90% identical to SEQ ID NO: 8 and having a 4'-O-glycosyltransferase activity is effected by introducing into the cell an exogenous nucleic acid sequence encoding a polypeptide comprising an amino acid sequence at least 90% identical to SEQ ID NO: 8.

As used herein, the term "polypeptide" refers to a linear organic polymer consisting of a large number of amino-acid residues bonded together by peptide bonds in a chain, forming part of (or the whole of) a protein molecule. The amino acid sequence of the polypeptide refers to the linear consecutive arrangement of the amino acids comprising the polypeptide, or a portion thereof.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein "expressing" refers to expression at the mRNA and optionally polypeptide level.

The term "endogenous" as used herein refers to any compound, polynucleotide or polypeptide which is naturally expressed within a cell from a wild type genomic location (e.g. plant cell, microorganism) and at wild type levels.

As used herein, the phrase "exogenous" refers to a polynucleotide or polypeptide which may not be naturally expressed within the cell (e.g., a nucleic acid sequence from a different species) or which overexpression in the cell (e.g. plant cell, microorganism) is desired.

When expressing an exogenous polynucleotide in a cell, the exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the cell (e.g. plant cell, microorganism).

Polynucleotides suitable for use with the methods of the invention include, but are not limited to, polynucleotides comprising a nucleic acid sequence encoding the amino acid sequence at least 90% identical to SEQ ID NO: 8, or functional homologs thereof.

Functional homologs of the polypeptides described above are also suitable for use in the methods described herein. A functional homolog is a polypeptide that has sequence similarity to a reference polypeptide, and that carries out one or more of the biochemical or physiological function(s) of the reference polypeptide. Thus, functional homologues of the enzymes described herein are polypeptides that have sequence similarity to the reference enzyme, and which are capable of catalyzing the same step or part of a step of the methods of the invention as the reference enzyme. According to one embodiment, a functional homologue of the enzyme described herein is a polypeptide capable of having a 4'-O-glycosyltransferase activity.

According to some embodiments of the invention, the polynucleotide of the invention comprises a nucleic acid sequence encoding a polypeptide comprising the amino acid sequence as set forth in SEQ ID NO: 8 or at least 90% identical or homologous thereto.

According to one embodiment, the polynucleotide of the invention comprises a nucleic acid sequence at least 90% identical to SEQ ID NO: 7. According to some embodiments, the polynucleotide comprises a nucleic acid sequence is at least 90% homologous to SEQ ID NO: 7.

According to one embodiment, the polynucleotide of the invention comprises a nucleic acid sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% homology or identity to SEQ ID NO: 7.

According to a specific embodiment, the polynucleotide of the invention comprises a nucleic acid sequence encoding a MdPh-4'-OGT polypeptide (i.e. comprising the amino acid sequence as set forth in SEQ ID NO: 8) is as set forth in SEQ ID NO: 7.

According to a specific embodiment, the polynucleotide of the invention comprises a nucleic acid sequence encoding a UDP-glucose:flavonoid 7-O-glucosyltransferase (as set forth in accession number AAX16493 and SEQ ID NO: 7).

According to one embodiment, upregulating in a plant expression of a polypeptide can be achieved by elevating the expression level of a native gene of a plant as compared to a control plant. This can be done for example, by means of genome editing which are further described hereinunder, e.g., by introducing mutation(s) in regulatory element(s) (e.g., an enhancer, a promoter, an untranslated region, an intronic region) which result upregulation of the native gene, and/or by Homology Directed Repair (HDR), e.g., for introducing a "repair template" encoding the polypeptide-of-interest.

Additionally and/or alternatively, upregulating in a plant expression of a polypeptide can be achieved by increasing a level of a polypeptide-of-interest due to expression of a exogenous polynucleotide by means of recombinant DNA technology, e.g., using a nucleic acid construct comprising a polynucleotide encoding the polypeptide-of-interest.

According to one embodiment, the exogenous polynucleotide is provided in a nucleic acid construct useful in transforming the host cell. As mentioned, suitable host cells include e.g. bacteria, yeast and other microorganisms, plant cells and other eukaryotic cells.

Constructs useful in the methods according to some embodiments of the invention may be constructed using recombinant DNA technology well known to persons skilled in the art. The gene constructs may be inserted into vectors, which may be commercially available, suitable for transforming into cells (e.g. plant cells) and suitable for expression of the gene of interest in the transformed cells. The genetic construct can be an expression vector wherein the nucleic acid sequence is operably linked to one or more regulatory sequences allowing expression in the cells (e.g. plant cells).

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
| --- | --- | --- |
| Actin | constitutive | McElroy et al, Plant Cell, 2: 163-171, 1990 |
| CAMV 35S | constitutive | Odell et al, Nature, 313: 810-812 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107-121, 1996 |

TABLE II

Exemplary seed-preferred promoters for use in the performance of some embodiments of the invention

| Gene Source | Expression Pattern | Reference |
| --- | --- | --- |
| Seed specific genes | seed | Simon, et al., Plant Mol, Biol. 5. 191, 1985; Scofield, et al., J. Biol Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet, 208: 15-22, 1986; Takaiwa, et al. FEBS Letts. 221: 43-47, 1987 |
| Zein | seed | Matzke et al Plant Mol Biol. 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltr1 promoter | endosperm | |
| barley B1, C, D hordein | endosperm | Theor Appl Gen 98: 1253-62, 1999; Plant J 4: 343-55, 1993; M Gen Genet 250: 750-60, 1996 |
| Barley DOF | endosperm | Mena et al, The Plant Journal, 116(1): 53-62, 1998 |
| Biz2 | endosperm | EP 99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice-globulin Glb-1 | endosperm | Wu et al, Plant Cell Physiology 398) 885-889, 1998 |
| rice OSH1 | embryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorgum gamma-kafirin | endosperm | PMB 32: 1029-35, 1996 |
| KNOX | embryo | Postma-Haarsma et al, Plant Mol Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, et al., Plant Mol. Biol. 19: 873-876, 1992 |

TABLE III

Exemplary flower-specific promoters for use in the performance of the invention

| Gene Source | Expression Pattern | Reference |
| --- | --- | --- |
| AtPRP4 | flowers | www(dot)salus(dot) medium(dot)edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |

TABLE IV

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme 1 | |
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | |
| PR00131 | GOS9 | Strong constitutive |
| PR00133 | chitinase Cht-3 | very weak meristem specific |
| PR00135 | alpha-globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PRO0228 | BLZ-2_long (barley) | |

According to one embodiment, constructs are used which allow expression of the polypeptide in plant tissues which comprise the substrates.

Nucleic acid sequences of the polypeptides of some embodiments of the invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot)or(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially to useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein. encoded by the modified nucleotide sequence is produced at a level higher than the protein encoded by the corresponding naturally occurring or native gene. Construction of synthetic genes by altering the codon usage is described in for example PCT Patent Application 93/07278.

Thus, some embodiments of the invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Plant cells may be transformed stabley or transiently with the nucleic acid constructs of some embodiments of the invention. In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) Agrobacterium-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Chang et al. Plant Cell Rep, (1988) 7:379-384, Fromm et al, Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the Agrobacterium delivery system in combination with vacuum infiltration. The Agrobacterium system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation. is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV). Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMI30 J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread is in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference, A polypeptide can thus be produced by the protein expression system of the chloroplast and become integrated into the chloroplast's inner membrane.

According to some embodiments of the invention, upregulating in a plant expression of a polypeptide of the invention is achieved by means of genome editing.

Genome editing is a powerful mean to impact target traits by modifications of the target plant genome sequence. Such modifications can result in new or modified alleles or regulatory elements. Thus, genome editing employs reverse genetics by artificially engineered nucleases to cut and create specific double-stranded breaks at a desired location (s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break. point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Since most genome-editing techniques can leave behind minimal traces of DNA alterations evident in a small number of nucleotides as compared to transgenic plants, crops created through gene editing could avoid the stringent regulation procedures commonly associated with genetically modified (GM) crop development.

Upregulating in a plant expression of a polypeptide by genome editing can be achieved by: (i) replacing an endogenous sequence encoding the polypeptide of interest or a regulatory sequence under the control which it is placed, and/or (ii) inserting a new gene encoding the polypeptide of interest in a targeted region of the genome, and/or (iii) introducing point mutations which result in up-regulation of the gene encoding the polypeptide of interest (e.g., by altering the regulatory sequences such as promoter, enhancers, 5'-UTR and/or 3'-UTR, or mutations in the coding sequence).

According to one embodiment, Homology Directed Repair (UDR) can be used to generate specific nucleotide changes (also known as gene "edits") ranging from a single nucleotide change to large insertions. The HDR method was successfully used for targeting a specific modification in a coding sequence of a gene in plants [Budhagatapalli Nagaveni et al. (2015) "Targeted Modification of Gene Function Exploiting Homology-Directed Repair of TALEN-Mediated Double-Strand Breaks in Barley". G3 (Bethesda). 2015 September; 5(9): 1857-1863; Zhao Yong ping et al. (2016) An alternative strategy for to targeted gene replacement in plants using a dual-sgRNA/Cas9 design. Scientific Reports 6, Article number: 23890 (2016)].

According to one embodiment, CRISPR-Cas system can be used for altering gene expression in plants as described in U.S. Patent Application publication No. 20150067922 to Yang; Yinong et al., which is fully incorporated herein by reference.

According to one embodiment, meganucleases can be used for altering gene expression in plants. Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety.

According to one embodiment, engineered nucleases, including zinc-finger nucleases (ZFNs) and transcription activator-like effector nucleases (TALENs), can be used for altering gene expression in plants by producing targeted double-stranded breaks (as described in Christian et al., 2010; Kim et al., 1996; Li et al., 2011; Mahfouz et al., 2011; Miller et al., 2010).

Genome editing can also be carried out using recombinant adeno-associated virus (rAAV) platform or using transposases.

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT).

According to some embodiments of the invention, there is provided a host cell heterologously expressing an isolated polynucleotide of the invention, as described hereinabove.

As mentioned above, the host cell can be any suitable cell including but not limited to, bacteria, yeast and other microorganisms that can be cultured or grown in fermentation, plant and other eukaryotic cells. For example, the host cell can be a bacterial cell (e.g., *E. coli* and *B. subtilis*) transformed with a heterologous nucleic acid, such as bacteriophage DNA, plasmid DNA, or cosmid DNA expression vectors containing the nucleic acid molecules described herein, or yeast (e.g., *S. cerevisiae* or *S. pombe*) transformed with recombinant yeast expression vectors containing the nucleic acid molecules described herein.

In some embodiments, the host cell produces trilobatin.

As mentioned above, trilobatin biosynthesis typically requires the co-substrates phloretin and UDR-glucose. Thus, according to one embodiment, the host cell comprises phloretin and UDP-glucose. The phloretin and UDP-glucose, each separately or combined, may be endogenous to the cell or added exogenously. Additionally, in order to upregulate production of trilobatin, the substrates (e.g. phloretin and/or UDP-glucose) may be added exogenously to cells comprising endogenous levels of these substrates. Such a step typically results in an increase of at least about 5%, 10%, 20%. 30%, 40%, 50%, 60%, 70%, 80%, 90%, 100%, or more in substrate levels (e.g. phloretin and/or UDP-glucose) as compared to a host cell not receiving the substrates exogenously.

Additionally or alternatively, in order to upregulate production of trilobatin, the substrates (e.g. phloretin and/or IMP-glucose) levels in a cell may be upregulated by increasing a level of a component in the phloretin and/or UDP-glucose biosynthesis pathways. Accordingly, for upregulated phloretin levels, naringin dihydrochalcone, phlorizin, phloretin-4'-O-glucoside or p-dihydrocoumaroyl-CoA levels may be upregulated. Alternatively, the level of Chalcone synthase or naringenin-chalcone synthase (CHS) may be upregulated along with the co-substrate 3× Malonyl-CoA for upregulated synthesis of phloretin. Likewise, for upregulated IMP-glucose levels, glucose-1-phosphate may be upregulated. Alternatively, the level of UDP-glucose-pyrophosphorylase may be upregulated along with the co-substrate UTP for upregulated synthesis of UDP-glucose.

Exogenous addition of a substrate (e.g. phloretin and/or UDP-glucose) may be effected using any method known in the art, such as by contacting the host cell with the substrates (e.g. phloretin and UDP-glucose), such as in a cell culture medium.

Expression of additional enzymes in a cell can be effected using nucleic acid constructs or using genome editing as described herein (e.g. for expression of a polypeptide comprising an amino acid sequence at least 90% identical to SEQ ID NO: 8 and having a 4'-O-glycosyltransferase activity). It will be appreciated that more than one exogenous polynucleotide (e.g. 2, 3, 4, 5, etc.) may be provided in a single nucleic acid construct, alternatively, two or more (e.g. 3, 4, 5, etc.) nucleic acid constructs may be introduced into a single host cell.

According to one embodiment, there is provided a transgenic plant or plant cell comprising an exogenous nucleic acid sequence encoding a polypeptide comprising an amino acid sequence at least 90% identical to SEQ ID NO: 8 and having a 4'-O-glycosyltransferase activity.

According to one embodiment, there is provided a method of producing a transgenic plant the method comprising introducing into cells of the plant a nucleic acid construct comprising a nucleic acid sequence encoding a polypeptide comprising an amino acid sequence at least 90% identical to SEQ ID NO: 8 and having a 4'-O-glycosyltransferase activity.

According to one embodiment, the cell (e.g. host cell), plant cell or plant comprise a substrate selected from the group consisting of phloretin, trilobatin, phloridzin, quercetin, naringenin and butein.

According to one embodiment, the cell (e.g. host cell), plant cell or plant comprises a UDP-glucose substrate.

According to one embodiment, the cell (e.g. host cell), plant cell or plant comprises a phloretin substrate and a UDP-glucose substrate.

According to one embodiment, when the cell (e.g. host cell), plant cell or plant comprises phloretin and UDP-glucose, the cell, plant cell or plant (e.g. transgenic plant) produces trilobatin.

As mentioned above, additional products can be produced using the enzyme of some embodiments of the invention (i.e. comprising an amino acid sequence at least 90% identical to SEQ ID NO: 8 and having a 4'-O-glycosyltransferase activity). Such products depend on the substratels.

Host cells described herein can be used in methods to produce trilobatin. For example, if the host cell is a microorganism (e.g. *E. coli*), the method can include growing the microorganism in a culture medium under conditions in which the enzyme catalyzing the step of the methods of the invention, e.g. 4'-O-glycosyltransferase (e.g. MdPh-4'-OGT), is expressed. The recombinant microorganism may be grown in a fed batch or continuous process. Typically, the recombinant microorganism is grown in a fermenter at a defined temperature(s) for a desired period of time. Such a determination is within the skill of a person of skill in the art.

Similarly, when the host cell is a plant cell (e.g. leaf cell, flower cell, fruit cell, stem cell etc. as discussed below), the method can include growing the plant cell in a culture medium under conditions in which the enzyme catalyzing the step of the methods of the invention, e.g. 4'-O-glycosyltransferase (e.g. MdTh-4'-OGT), is expressed. The recombinant plant cell may be grown in a fed batch or continuous process. Typically, the recombinant plant cell is grown in a cell culture dish at a defined temperature(s) for a desired period of time. Such a determination is within the skill of a person of skill in the art.

According to one embodiment, additional products can be produced using the enzyme of some embodiments of the invention (i.e. comprising an amino acid sequence at least 90% identical to SEQ ID NO: 8 and having a 4'-O-glycosyltransferase activity). Such products depend on the substrate/s being used. Additional substrates contemplated by the present invention include, but are not limited to, trilobatin, phloridzin, quercetin, naringenin, epicatechin, cyanidin, 4-coumaric acid and caffeic acid.

The levels of the polypeptide (e.g. comprising an amino acid sequence at least 90% identical to SEQ ID NO: 8 and having a 4'-O-glycosyltransferase activity), substrates (e.g. phloretin or UDP-glucose) and products (e.g. trilobatin) can be determined in a host cell using any method known in the art. For example, samples may be obtained from a culture media or from a lysate of the host cells (discussed below) for analysis according to well-known methods, such as but not limited to ELISA and Western blotting (e.g. for measuring polypeptide levels), or using purification methods (discussed below).

According to one embodiment, a cell lysate can be prepared from the host cells expressing the enzyme of the invention (i.e. comprising an amino acid sequence at least 90% identical to SEQ ID NO: 8 and having a 4'-O-glycosyltransferase activity) and be used to contact a substrate, such phloretin and UDP-glucose, to produce trilobatin (e.g. in vitro).

Typically a cell lysate is obtained by physical disruption or detergent-based lysis of the host cells. Thus, for example, a cell lysate may be obtained by sonication, homogenization, enzymatic lysis using lysozyme, or by freezing and grinding of the host cells.

According to one embodiment, the cell lysate comprises a polynucleotide (exogenous) encoding a polypeptide comprising a 4'-O-glycosyltransferase activity (e.g. MdPh-4'-OGT).

According to one embodiment, the cell lysate comprises substrates (e.g. phloretin and/or UDP-glucose).

According to one embodiment, the cell lysate comprises trilobatin.

According to one embodiment, the cell lysate can be used for cell-free production of trilobatin, alone or in combination with other suitable substrates or enzymes.

According to one embodiment, the cell lysate can be used either for recovery of the products (e.g. trilobatin), for recovery of the recombinantly expressed polypeptides (e.g. MdPh-4'-OGT) or for recovery of the substrates (e.g. phloretin and/or UDP-glucose).

Methods for extraction of active enzyme polypeptides are well known in the art (e.g. Sasidharan S. et al. *Afr J Tradit Complement Altern Med.* (2011) 8(1): 1-10, incorporated herein by reference].

Methods of assaying 4'-O-glycosyltransferase activity are well known in the art and include, for example, standard glycosyltransferase enzyme assay for LC-MS and radioactive assay for the enzyme UDP-glucose pyrophosphorylase.

Methods for purifying the products (e.g. trilobatin) or substrates (e.g. phloretin and/or UDP-glucose) are well known in the art and include, for example, affinity purification, filtration, centrifugation, evaporation, liquid-liquid extraction, fractionation distillation.

Methods of measuring the level of the products (e.g. trilobatin) or substrates (e.g. phloretin and/or UDP-glucose) are well known in the art and include, for example, one- and two-dimensional NMR.

The term "plant" as used herein encompasses whole plants, a grafted plant, ancestors and progeny of the plants and plant parts, including seeds, shoots, stems, roots (including tubers), rootstock, scion, leaves (including young leaves and mature leaves), flowers, fruit (including skin and flesh), plant cells, tissues and organs. The plant may be in any form including suspension cultures, embryos, meristematic regions, callus tissue, leaves, gametophytes, sporophytes, pollen, and microspores.

The term "plant cell" as used herein encompasses a cell of any plant or plant part including, but not limited to, a cell of a leaf (including a young leaf and a mature leaf), cell of a flower, a cell of a fruit (including cell of a skin or a flesh of the fruit), a cell of a root, a cell of a rootstock, a cell of a stem, a cell of a shoot, a cell of a seed, and a meristem.

Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia frauans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochioa pyramidalis, Ehraffia* spp., *Eleusine coracana, Eragrestis* spp., *Erythrina* spp., *Eucalypfus* spp., *Euclea schimperi, Eulalia villosa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypefthelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffliria squarrosa, Populus* spp., *Prosopis cineraria, Pseudotsuga menziesii, Pterolobium steilatum, Pyrus communis, Quercus* spp., *Rhaphiolepsis umbellata, Rhopalostylis sapida, Rims natalensis, Ribes grossularia, Ribes* spp., *Robinia pseudoacacia, Rosa* spp., *Rubus* spp., *Salix* spp., *Schyzachyriurn sanguineurn, Sciadopitys vefficillata, Sequoia sernpervirens, Sequoiadendron giganteum, Sorghum bicolor, Spinacia* spp., *Sporobolus fimbriatus, Stihurus alopecuroides, Stylosanthos humilis, Tadehagi* spp, *Taxodium distichum, Themeda triandra, Trifolium* spp., *Triticum* spp., *Tsuga heterophylla, Vaccinium* spp. *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Vindiplantae can be used for the methods of some embodiments of the invention. In one embodiment, the plant is a plant of the Cucurbitaceae family, such as *S. grosvenorii.*

According to one embodiment, the plant is a plant of the Rosaceae family, such as but not limited to, apple tree, pear tree, quince tree, apricot tree, plum tree, cherry tree, peach tree, raspberry bush, loquat tree, strawberry plant, almond tree, and ornamental trees and shrubs (e.g. roses, meadowsweets, photinias, firethorns, rowans, and hawthorns).

According to one embodiment, the plant is a plant of a *Vitis* species. Exemplary *Vitis* species include, but are not limited to, *Vitis piasezkii maxim* and *Vitis succharifera makino,*

According to one embodiment, the plant is a plant of the genus *Malus.* Exemplary *Malus* species include, but are not limited to, *Malus aldenhamii Malus angustifolia, Malus asiatica, Malus baccata, Malus coronaria, Malus domestica, Malus doumeri, Malus florentina, Malus floribunda, Malus furca, Malus halliana, Malus honanensis, Malus hupehensis, Malus ioensis, Malus kansuensis, Malus mandshurica, Malus micromalus, Malus niedzwetzkyana, Malus ombrophilia, Malus orientalis, Malus prattii, Malus pruni-* folia, *Malus pumila*, *Malus sargentii*, *Malus sieboldii*, *Malus sieversii*, *Malus sylvestris*, *Malus toringoides*, *Malus transitoria*, *Malus trilobata*, *Malus tschonoskii*, *Malus*.times.*domestica*, *Malus*.times.*domestica*.times.*Malus sieversii*, *Malus sylvestris*, *Malus*.times.*domestica*.times.*Pyrus communis*, *Malus xiaojinensis*, *Malus yunnanensis*, *Malus* sp. and *Mespilus germanica*, In a specific embodiment, the plant is a *Malus domestica*, *Malus trilobata* or *Malus sieboldii*.

In a specific embodiment, the plant is a plant of the genus *Smilax* (e.g. *Smilax glyciphylla*), *Lithocarpus* (e.g. *Lithocarpus polystachyus*) or *Fragaria*.

As mentioned, the method of some embodiments of the invention generated plants producing trilobatin. The plant may be a plant which does not naturally produce trilobatin, or alternatively, may be a plant which comprises endogenous levels of trilobatin which are upregulated by the methods of some embodiments of the invention.

According to a specific embodiment, the plant does not comprise detectable levels of endogenous trilobatin (e.g., as measured by LC-MS and NMR spectrum).

Increase in trilobatin levels may be by at least about 5%, 10%, 20%, 30%, 40%, 50%, 60%, 70%, 80%, 90%, 100%, or more as compared to a plant not treated by the methods of some embodiments of the invention.

The method of generating a plant which produces trilobatin is effected by upregulating in the plant expression of a polypeptide comprising an amino acid sequence at least 90% identical to SEQ ID NO: 8 and having a 4'-O-glycosyltransferase activity.

Upregulating in the plant expression of the polypeptide comprising an amino acid sequence at least 90% identical to SEQ ID NO: 8 and having a 4'-O-glycosyltransferase activity may be by at least about 5%, 10%, 20%, 30%, 40%, 50%, 60%, 70%, 80%, 90%, 100%, or more as compared to a plant not treated by the methods of some embodiments of the invention.

Thus, according to one embodiment, increasing trilobatin content in a plant involves the transformation of at least one plant cell with a construct designed to upregulate expression of a polypeptide comprising an amino acid sequence at least 90% identical to SEQ ID NO: 8 and having a 4'-O-glycosyltransferase activity (as discussed above). Expression in a plant cell of the polypeptide comprising an amino acid sequence at least 90% identical to SEQ ID NO: 8 and having a 4'-O-glycosyltransferase activity, in the presence of trilobatin substrates (e.g. phloretin and UDP-glucose), upregulates trilobatin content in such plant cells. Assessment of the trilobatin content in a plant may be verified by measuring trilobatin levels (e.g., by LC-MS and NMR spectrum).

According to specific embodiments the development and growth of the genetically modified plant is not affected. Evaluating development and growth of a plant may be effected by determining e.g. fruit ripening, organ growth, cell division, cell elongation, senescence, germination, respiration, photosynthesis, transpiration, flowering, pollination and fertilization.

According to another embodiment, increasing trilobatin content in a plant may involve breeding with a plant which expresses the polypeptide comprising an amino acid sequence at least 90% identical to SEQ ID NO: 8 and has a 4'-O-glycosyltransferase activity. Such a plant may be a plant which naturally expresses a polypeptide comprising an amino acid sequence at least 90% identical to SEQ ID NO: 8 and having a 4'-O-glycosyltransferase activity. Alternatively, the plant may be a transgenic plant transformed to express a polypeptide comprising an amino acid sequence at least 90% identical to SEQ ID NO: 8 and having a 4'-O-glycosyltransferase activity (e.g. such as described above).

According to some embodiments of the invention, breeding is effected such that the genome of the recipient is at least 95%-99% that of the recipient and 5% or down to 1% that of the donor (comprising the genomic sequence encoding SEQ ID NO: 8 or sequence at least 90% identical to SEQ ID NO: 8 and having a 4'-O-glycosyltransferase activity (e.g. such as described above)). Such progeny typically involve pedigree programs involving backcrossing and selection as described herein.

As used herein, the phrase "transgenic plant" refers to a plant in which one or more of the cells of the plant is stably or transiently transformed with an exogenous polynucleotide sequence introduced by way of human intervention (e.g. by genetic engineering of the plant). Transgenic plants typically express DNA sequences, which confer the plants with characters different from that of native, non-transgenic plants of the same strain.

Thus, according to an embodiment of the present invention, a first plant (i.e. not expressing a polypeptide comprising an amino acid sequence at least 90% identical to SEQ ID NO: 8 and having a 4'-O-glycosyltransferase activity) can be crossed with a second plant (i.e. expressing a polypeptide comprising an amino acid sequence at least 90% identical to SEQ ID NO: 8 and having a 4'-O-glycosyltransferase activity).

It should be noted that although the above described plant breeding approach utilize one transformed plant and one untransformed plant, approaches which utilize two or more individually transformed plants, each comprising one or two components (e.g. polypeptides, substrates, etc.) can also be utilized. Thus, plants which are modified to express more than one transgene may be the outcome of crossing a first transgenic plant expressing transgene (a), with a second transgenic plant expressing transgene (b) and selection of a plant progeny which expresses transgenes (a+b).

According to another embodiment, increasing trilobatin content in a plant may involve crossing two non-transgenic plants, for instance one apple plant and one pear plant, wherein at least one of the plants expresses the polypeptide comprising an amino acid sequence at least 90% identical to SEQ ID NO: 8 and has a 4'-O-glycosyltransferase activity.

Crossing and breeding can be accomplished by any means known in the art for breeding plants such as, for example, cross pollination of the first and second plants that are described above and selection for plants from subsequent generations which express a polypeptide comprising an amino acid sequence at least 90% identical to SEQ ID NO: 8 and having a 4'-O-glycosyltransferase activity and produce trilobatin. The plant breeding methods used herein are well known to one skilled in the art. For a discussion of plant breeding techniques, see Poehlman (1987) Breeding Field Crops, AVI Publication Co., Westport Conn. Many crop plants useful in this method are bred through techniques that take advantage of the plant's method of pollination.

Crossing and breeding can further be accomplished by cross breeding plants of different breeds, varieties, species or genera. For example, a hybrid between species from different genera (intergeneric hybrid) can comprise a hybrid of cultivated apple (*Malus*×*domestica*) and European pear (*Pyrus communis*), a hybrid of apple (*Malus*) and Sorbus, a hybrid of wood apple (*Malus sylvestris*) and wild service tree (*Sorbus torminalis*), or a hybrid of pear (*Pyrus*) and quince (*Cydonia oblonga*) (additional examples are provided in www(dot)agroforestry(dot)co(dot)uk/wp-content-luploads/agnews-sample/AGN_sample(dot)pdf, incorporated herein by reference). Alternatively, a hybrid between species from the same genera (interspecific hybrid) includes, but is not limited to, a hybrid between *Malus baccata* and *Malus domestica*, a hybrid between *Malus coronaria* and *Malus domestica*, or a hybrid between *Malus prunifolia* and *Malus domestica* (additional examples are provided in vvvvvv(dot)inspection(dot)gc(dot)ca/plants/plants-with-novel-traits/applicants/directive-94-08/biology-documents/malus-domestica/eng/1404417088821/1404417158789?chap=5, incorporated herein by reference).

It will be appreciated that when referring to a genetically modified plant or plant cell, the present inventors also refer to progeny arising therefrom.

Progeny resulting from breeding or alternatively multiple-transformed plants can be selected, by verifying presence of a 4'-O-glycosyltransferase activity or by measuring the level of trilobatin produced by the plants (as described above). Such methods may be applied at a young age or early developmental stage when the altered 4'-O-glycosyltransferase activity or trilobatin content may not necessarily be easily measurable.

Once trilobatin producing progeny are identified, such plants are further cultivated under conditions which maximize production of trilobatin. It will be appreciated that such conditions may differ between plant species and between different environmental growth areas and climates.

According to one embodiment of the invention, trilobatin can be produced using in vitro methods i.e., cell-free. Accordingly, the enzyme of the invention (i.e. comprising an amino acid sequence at least 90% identical to SEQ ID NO: 8 and having a 4'-O-glycosyltransferase activity) can be contacted with a substrate, such phloretin and UDP-glucose, under conditions in which the enzyme catalyzes the attachment of a glucose moiety to a phloretin at the 4-hydroxyl group to produce trilobatin. One of ordinary skill in the art is capable of determining the amount of enzyme, the amount of substrates, and the conditions used to produce trilobatin.

According to one embodiment, trilobatin in the reaction mixture is used as is i.e., without further purification. According to another embodiment, trilobatin is purified from the mixture using methods well known in the art. For example, trilobatin may be purified by affinity purification, filtration, centrifugation, evaporation, liquid-liquid extraction, fractionation and distillation.

Methods of measuring the level of the trilobatin are well known in the art and include, for example, one- and two-dimensional NMR.

The present invention further comprises compositions comprising trilobatin.

Compositions comprising trilobatin can be obtained from a cell lysate (as discussed above). Additionally or alternatively, compositions comprising trilobatin can be obtained from plants producing trilobatin.

Trilobatin may be extracted from plants by different methods known to those skilled in the art. For example, Tanaka T, et al. Isolation of Trilobatin, a Sweet Dihydrochalcone-Glucoside from Leaves of *Vitis piasezkii* Maxim. and *V. saccharifera* Makino, *Agricultural and Biological Chemistry*, (1983) 47:10, 2403-2404 (incorporated herein by reference) provide methods of isolation of trilobatin from Vitis leaves. Furthermore, Xiang-Dong Qin and Ji-Kai Liu Z., *Naturforsch.* (2003) 58c, 759-761 (incorporated herein by reference) provide methods of isolation of trilobatin from leaves of *Lithocarpus pachyphyllus*.

According to one embodiment, there is provided a composition comprising trilobatin generated according to the method of some embodiments of the invention.

In some embodiments, the composition of the invention is a consumable composition.

Consumables include all food or feed products, including but not limited to, cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof.

Trilobatin compositions of the invention can be used in various consumables including but not limited to water-based consumables, solid dry consumables and dairy products, dairy-derived products and dairy-alternative products. In some embodiments the composition is a foodstuff.

Accordingly, the trilobatin compositions may be in a form selected from a granulated form, a powder form, a paste form and a liquid form.

Water-based consumables include but are not limited to beverage, water, aqueous drink, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacao (water-based), tea-based drink, coffee-based drink, cacao-based drink, syrup, frozen fruit, frozen fruit juice, water-based ice, fruit ice, sorbet, dressing, salad dressing, sauce, soup, and beverage botanical materials (whole or ground), or instant powder for reconstitution (coffee beans, ground coffee, instant coffee, cacao beans, cacao powder, instant cacao, tea leaves, instant tea powder). In some embodiments, the composition can be a beverage such as Coca-Cola®, Pepsi® and the like.

Solid dry consumables include but are not limited to cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, and botanical materials (whole or ground), and instant powders for reconstitution as mentioned above.

For water-based or solid dry consumables a useful concentration may be from about 5 ppm to about 100 ppm, from about 5 ppm to about 500 ppm, from about 5 ppm to about 1000 ppm, from about 50 ppm to about 100 ppm, from about 50 ppm to about 500 ppm, from about 50 ppm to about 1000 ppm, from about 100 ppm to about 500 ppm, from about 100 ppm to about 1000 ppm, from about 250 ppm to about 500 ppm, from about 250 ppm to about 750 ppm, from about 250 ppm to about 1000 ppm, from about 500 ppm to about 750 ppm, from about 500 ppm to about 1000 ppm or more.

According to a specific embodiment, for water-based or solid dry consumables a useful concentration may be from about 5 ppm to about 500 ppm.

For human or animal consumption, the trilobatin compositions are typically free of contaminants (e.g. microbial contaminants). Thus, the trilobatin compositions are suitable for human (or animal) consumption.

Trilobatin has been previously described as a natural sweetener and a bitter blocker. Accordingly, the trilobatin compositions can be used as sweetener compositions, bitterness blocker compositions and flavor enhancer compositions in the food, feed, beverage and pharmaceutical industries.

In some embodiments, taste modifiers comprising trilobatin may be added to another composition that includes one or more sweetener components (e.g. sucrose) or bitterness Mockers. Determination of the amount of trilobatin to be added to each composition is within the skill of a person of skill in the art. For example, in certain products a higher sweetener concentration is usually necessary to reach similar sweetness intensity, for example in dairy products.

The composition of the invention can also include one or more additional flavor ingredients. A non-limiting list of suitable flavor ingredients useful with the composition of the invention includes sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, stevia and trilobtain.

The composition of the invention can also include one or more additional additives such as, for example, colors, preservatives, nutritive additives such as vitamins and minerals, condiments, amino acids (i.e. essential amino acids), emulsifiers, pH control agents such as acidulants, hydrocolloids, antifoams and release agents, flour improving or strengthening agents, raising or leavening agents, cohesive agents, gases and chelating agents, the utility and effects of which are well-known in the art. See Merriani-Webster's Collegiate Dictionary, 10th Edition, 1993.

Compositions comprising the extracts or compounds of the present invention can be further formulated for administration as dietary supplements using one or more consumable carriers. A "consumable carrier" is herein defined as any food, food ingredient, or food additive, or any excipient utilized for tabletting, encapsulation, or other formulation of an active agent for oral administration, whether for human or animal use. Specific additives are well known to those of skill and are listed in places such as the U.S. Pharmacopeia. For dietary supplements, the extract can be mixed according to methods routine in the art. Dietary supplements can be prepared in a variety of forms including, but not limited to, liquid, powder, or solid pill forms.

The trilobatin compositions may be consumed for general health, but may be especially advantage to subjects susceptible to conditions associated with oxidative stress, such as artherosclerosis, diabetes, cancer, cardiovascular disease, liver disease and individuals at risk of developing neurodegenerative diseases such as Alzheimer's disease, or to subjects exposed to carcingens.

According to one embodiment, the trilobatin compositions comprise anti-oxidative activity (i.e. the act of neutralizing free radicals such as those found in a physiological environment).

According to one embodiment, the trilobatin compositions comprise anti-carcinogenic activity (i.e. counteract the effects of a carcinogen including e.g. a substance, a radionuclide, or a radiation involved in causing cancer).

Accordingly, the compositions comprising trilobatin of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the trilobatin accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Pharmaceutical compositions suitable for use in context of some embodiments of the invention include compositions wherein the active ingredients are contained in an amount effective to achieve the intended purpose. More specifically, a therapeutically effective amount means an amount of active ingredients (trilobatin) effective to prevent, alleviate or ameliorate symptoms of a disorder (e.g., cardiovascular disease, diabetes, carcinogenic disease, neurodegenerative disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1). Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert, Compositions comprising a preparation of the invention formulated in a compatible pharmaceutical carrier may also be prepared, placed in an appropriate container, and labeled for treatment of an indicated condition, as is further detailed above.

The term "treatment" or "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age or gender which suffer from the pathology. According to one embodiment, this term encompasses individuals who are at risk to develop the pathology.

According to one embodiment, the pharmaceutical composition is for use for the treatment of a carcinogenic disease. Accordingly, the trilobatin compositions of some embodiments of the invention counteract the effects of a carcinogen (e.g. a substance, a radionuclide, or a radiation involved in causing cancer) and/or inhibit the development of cancer. Exemplary cancers include, without being limited to, colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, phyllodes tumor, Ewing's sarcoma, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, or lymphoma.

According to one embodiment, the pharmaceutical composition is for use for the treatment of a cardiovascular disease (e.g. myocardial infarction).

According to one embodiment, the pharmaceutical composition is for use for the treatment of diabetes mellitus (e.g. diabetes type I, diabetes type II, metabolic syndrome, diabetic vasculopathy).

According to one embodiment, the pharmaceutical composition is for use for the treatment of a neurodegenerative disease (e.g. Alzheimer's disease, Parkinson's disease, Multiple Sclerosis. Amyotrophic Lateral Sclerosis (ALS), multisystem atrophy, stroke, epilepsy, Pick's disease, Spinal-cerebellar ataxia, Huntington's disease, progressive supranuclear palsy, progressive supernuclear palsy, granulovacuolar disease, frontotemporal dementia, corticobasal degeneration, epilepsy, autoimmune encephalomyelitis, diabetic neuropathy, glaucomatous neuropathy, Lewy Body disease, Creutzfeld-Jacob Disease (CJD), variant Creutzfeld-Jacob Disease, new variant Creutzfeld-Jacob Disease, or kuru disease).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 7 is expressed in a DNA sequence format (e.g., reciting T for thymine), but it can refer to either a DNA sequence or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols, 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" flames, B. D., and Higgins S. J., eds. (1985); "Transcription and Translation" flames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND EXPERIMENTAL PROCEDURES

Chemicals

HPLC-grade acetonitrile, isopropyl-1-thio-β-D-galactopyranoside (IPTG), methanol, phloretin, butein, cyanidin, cyanidin-3-O-glucoside, cyanidin-5,3-O-glucoside and other chemical standards were purchased from Sigma-Aldrich. Trilobatin, quercetin-7-O-glucoside, and naringenin-O-glucoside were obtained from Extrasynthese (Genay Cedex, France, www(dot)extrasynthese(dot)com).

Plant Materials

Flower tissues (fully open), young and mature leaves, and fruit tissue of different developmental stages of Malus× domestica "Golden delicious" were collected from the Apple germplasm at Newe Yaar Research Center. Developmental stages were defined as is previously reported by Costa et al. [Costa F. et al., J. Exp. Bot. (2010) 61: 3029-3039]:"Early Green" (stage 1; 30 days after bloom), "Breaker" (stage 3), "Ripening" (stage 4). Fruits were peeled with a razor blade to carefully separate the skin from the flesh. All plant materials were flash-frozen and stored at −80° C. until use.

Data Mining and Phylogenetic Analysis

All sequences in the www(dot)rosaceae(do org database that were similar to YjiC glycosyltransferase from Bacillus licheniformic [Pandey R. P. et al., Appl. Environ. Micrab. (2013) 79, 3516-3521] were translated using the bioinformatics resource "ExPASy" server (www(dot)expasy(dot) org) and were reassembled using the CAP3 sequence assembly program. The resulting candidate sequences were compared to the UDP-glycosyltransferase from Bacillus licheniformic and each other using BlastP. An unrooted neighbor-joining tree of the MdPh-4'-OGT amino acid sequence and different homologous plant proteins were generated using the Phylogeny Analysis MEGA6 program. The resulting tree was bootstrap-analyzed with 1000 replicates.

Cloning and Expression of a cDNA of the MdPh-4'-OGT

Based on sequence information, two specific primers were designed corresponding to the 5'-end (5'-ATG GTG CAA CAC CGC TTT CTA C-3', SEQ ID NO: 1) and 3'-end (5'-GTG CCT AGC ATC TTT TAA AAC CTT GAT CTG-3', SEQ ID NO: 2) of the apple MdPh-4'-OGT nucleotide sequence. RNA from apple fruits and leaves was isolated using the Qiagen RNeasy kit (Hilden, Germany). For cloning, 5 μg of total RNA were reverse transcribed with RevertAid First Strand cDNA Synthesis Kit (Thermo scientific) and the corresponding cDNA was amplified to yield a fragment of approximately 1446-bp.

The cDNA was ligated into the pEXP5-NT/TOPO TA expression vector (Invitrogen Corporation, Carlsbad, Calif., USA.) to create a fusion of the open-reading frame with a His tag-coding extension at the N-terminus and transformed into E. coli Top10 cells. The constructs were verified by sequencing using the T7 promoter primers. The expression constructs were then introduced into E. coli strain BL21 (DE3) (Invitrogen). A 3 ml pre-culture was grown overnight at, 37° C. in an LB medium containing 100 μg·ml$^{-1}$ ampicillin (amp) and 34 μg·ml$^{-1}$ chloramphenicol.

This culture was used to inoculate 500 ml of fresh medium to which 1 mM isopropyl-1-thio-β-D-galactopyranoside (IPTG) was added to induce protein expression when the culture reached a density of $OD_{600}$ of 0.8. Cells were then grown for 12 hours at 16° C. After centrifugation for 10 minutes at 11,000×g, the cells were resuspended in a 50 mM Tris-HCl buffer containing 10% glycerol and 1 mM 2-mercaptoethanol (pH 7.5). Cells were lysed by a combination of a 20 minutes lysozyme treatment (1 mg per 500 ml of culture) and subsequent ultrasonication.

The supernatant containing the soluble recombinant MdPh-4'OGT protein was subjected to metal (nickel) affinity chromatography (Qiagen, Valencia, Calif., USA) with a stepwise gradient of increasing imidazole concentrations using standard procedures. The MdPh-4'O-GT containing fractions were pooled and desalted with a 50 mM Tris-HCl buffer containing 10% glycerol and 1 mM 2-mercaptoethanol (pH 7.5), using Vivaspin 20 (GE Healthcare, MWCO [molecular mass cut-off] of 10 kDa).

Protein concentrations were determined by the using Bradford reagent obtained from Sigma-Aldrich. The concentrated protein was assayed for glucosyltransferase activity and in parallel by SDS-PAGE.

MdPh-4'-OGT Transcript Analysis

For quantitative RT-PCR (qRT-PCR) analysis of MdPh-4'OGT, total RNA (5 μg) from different Malus tissues was extracted (Spectrum Plant Total RNA Kit, Sigma-Aldrich) and reverse-transcribed using an oligo primer and the RevertAid First Strand cDNA Synthesis Kit (Thermo Scientific, Israel).

qRT-PCR was performed on an Applied Biosystem StepOnePlus™ Real-Time PCR Systems (Life Technologies) using Absolute™ Blue qPCR SYBR® Green ROX Mix (Tamar Laboratory Supplies ltd, Israel), 5 ng reverse-translated total RNA, and 100 ng of each primers. Primers for MdPh-4'-OGT were MdPh-4'OGT _F-qPCR (5'-CGA TAA CGA GGC GAA GAA AGA-3', SEQ ID NO: 3) and MdPh-4'OGT _R-qPCR (5'-GAG AAC CTC CAC TTG ACT ACA C-3', SEQ ID NO: 4).

A relative quantification of gene expression was performed using the housekeeping gene actin from Malus as a reference gene. The primers used for actin were Malus-actin-F-qPCR: 5'-TCG TCC GTG GAG AAG AGT TA-3', SEQ ID NO: 5) and Malus-actin-R-qPCR: (5'-AAT CAT GGA TGG CTG GAA GAG-3', SEQ ID NO: 6). The difference in relative expression levels of MdPh-4'-OGT were calculated from $2^{-\Delta\Delta Ct}$ value after normalization of MdPh-4'-OGT data to actin. All analyses were performed using at least three biological replicates.

Standard Glucosyltransferase Enzyme Assay for LC-MS

MdPh-4'-OGT activity assays were performed in triplicate in 100 μL reactions using 500 ng His-tag purified (high purity level) recombinant MdPh-4'OGT protein. Reactions were performed in a glycosyltransferase buffer (50 mM Tris-HCl pH 7.5, and 2 mM 2-mercptoethanol), with 30 μM phioretin and 2 mM UDP-glucose. Reactions were performed at 30° C. for 60 minutes and terminated by addition of 10 μL of 10% TCA (v/v). Two microliters of the reaction products were used for analysis and identification by LC-UV-MS. All assay series were carried out at least in triplicate.

LC-TOF-MS Analysis

The UPLC-MS analysis was carried out on an Agilent 1290 Infinity series liquid chromatograph coupled with an Agilent 1290 Infinity DAD and Agilent 6224 Accurate Mass Time of Flight mass spectrometer (MS) (Agilent Technologies, Santa Clara, USA). The analytical column was a Zorbax Extend-C18 Rapid Resolution HT column (2.1×50.0 mm, 1.8 μm, Agilent Technologies, Waldbronn, Germany). The gradient elution mobile phase consisted of $H_2O$ with 0.1% (v/v) formic acid (eluent A) and acetonitrile containing 0.1% (v/v) formic acid (eluent B). The column was equilibrated with 10% B for 1.5 minutes. Eluent B was then increased to 95% till 12 minutes, and restored to 10% by 15 minutes. The flow rate of the mobile phase was 0.3 ml/min and the column oven temperature was 40° C. Eluting compounds were subjected to a dual-sprayer orthogonal ESI source, with one sprayer for analytical flow and one for the reference compound (Agilent Technologies, Santa Clara, USA). The ESI source was operated in negative mode with the following settings: gas temp of 300° C. with a flow of 8 L/min and nebulizer set to 35 psig. VCap set to 3000 V, the fragmentor to −140 V and the skimmer to 65 V. Scan mode of the mass detector was applied (100-1700 m/z) with a rate of 1 spectra/sec. The [M-H] ions of target compounds were detected using the 'find compound by formula' function and analyzed by Masshunter qualitative and quantitative analysis software version B.07.00 (Agilent technologies). Compounds were identified by comparison of exact mass and retention time to purchased standards.

Characterization of Heterologously Expressed MdPh-4'-OGT

All data included represent an average of at least three independent experiments. Determination of the pH optima within the range of 4.0-10.0 by mixing the stock buffer of 0.5 M citric acid and 1 M dibasic sodium phosphate solutions (for pH 4.0-7.0) and Tris-HCl (for pH 8.0-10.0), and the temperature optima within the range of 20° C.-45° C. (5° C. increments), respectively, were performed as described for the standard glycosyltransferase enzyme assay with phloretin as substrate and in the presence of UDP-glucose.

The apparent $K_m$ value for phloretin was determined by variation the phloretin concentrations from 0.5-500 μM with a fixed UDP-glucose concentration of 2 mM UDP-glucose, and 500 ng His-tag purified recombinant MdPh-4'-OGT protein. The $K_m$ value for UDP-glucose was determined by variation UDP-glucose concentration from 0.01-50 mM UDP-glucose with a fixed phloretin concentration of 30 μM, and 500 ng His-tag purified recombinant MdPh-4'-OGT protein.

The substrate specificity of MdPh-4'-OGT were performed as described for the standard glycosyltransferase enzyme assay using different substrates, and in the presence of IMP-glucose as the sugar donor. The activity with phloretin was arbitrarily set at 100%, and the relative conversion rates of the other substrates were calculated.

Example 1

A Bioinformatic Screen for 4'-O-Glycosyltransferase Genes from Apple

The existence of trilobatin (illustrated by no. 6 in FIGS. 1 and 4) was previously reported in *Malus* and in various other plants [Jugde H. et al., *FEBS J.* (2008) 275: 3804-3814; Dugé de Bernonville T. et al., *Phytochemistry* (2010) 71: 443-452; Gosch C. et al., *Plant Sci.* (2010) 178: 299-306]. However, neither glucosyltransferase (GT) enzymes nor their encoding genes that catalyzed the specific reaction of trilobatin have been isolated and characterized from *Malus* or other plant species. The present inventor took advantage of the sequence of the recently described GT from *B. licheniformic* (YjiC) that specializes in 4'-O glycosylation [Pandey R. P. et al., (2013), supra], as to screen available EST and genome databases of apple for a potential 4'-O-glycosyltransferase encoding gene involved in the biosynthesis of the natural dihydrochalcone sweetener trilobatin.

More than 20 candidate GT genes were thus identified in the *Malus* genome. Most of the potential *Malus* GTs shared less than 40% amino acid sequence identity with YjiC glycosyltransferase protein from *B. lichenlformic*. However, in the *Malus* genome there are at least 60 genes encoding proteins with similarity to UDP-glucosyltransferase. These include the two previously characterized phloretin 2'-O-glycosyltrannsferase from *M. domestica* and *Pyrus communis*, which convert phloretin into phloretin 2'-O-glucoside is (phloridzin).

Alignment of several *Malus* GT sequences with YjiC glycosyltransferase showed several highly conserved regions only in UDP-glucose:flavonoid 7-O-glucosyltransferase (accession number AAX16493) and *M. domestica* anthocyanidin 5,3-OGT, respectively (FIG. 8). The present inventor then generated cDNAs for the UDP-glucose:flavonoid 7-O-glucosyltransferase termed *Malus×domestica* UDP-glucose:phloretin 4'-O-glycosyltransferase (MdPh-4'-OGT) (as set forth in SEQ ID Nos: 7 and 8 for nucleic acid and amino acid sequences, respectively) (FIG. 7), and *M. domestica* anthocyanidin 5,3-OGT from RNA isolated from apple fruits (as set forth in SEQ ID Nos: 11 and 12 for nucleic acid and amino acid sequences, respectively). His-tagged recombinant proteins for two full-length apple UGT sequences were tested for their ability to glycosylate phloretin in the presence of UDP-glucose. Only MdPh-4'-OGT, of the two apple UGT proteins, was shown to possess phloretin glycosyltransferase activity to form trilobatin.

On the basis of the protein sequences and function, plant glycosyltransferases have been previously classified into 94 families numbered from GT1 to GT94 according to their sequences, motives, stereochemistry of the glycoside linkage, and known target specificity [Hansen, S. F. et al., *Front. plant Sci.* (2012) 3:59]. The GT1 family includes UDP-GTs common in plants, animals, fungi, and bacteria, which are responsible for the glycosylation of a variety of important organic structures, such as flavonoids, anthocyanins, terpenes, cofactors, steroids, and peptide antibiotics, making this one of the most intensely studied families of glycosyltransferases.

A phylogenetic tree was constructed using MdPh-4'-OGT and representative members of *Malus* phloretin 2'-OGT, and many other plant UDP-GT's of family 1, including some bacterial UDP-glucosyltransferase proteins (FIG. 2). MdPh-4'-OGT clusters together with several other GT-encoding sequences from the *Rosacea*, including *Fragaria ananassa*, *Pyres bretschneideri* crocetin GT, and *P. communis* flavonoid 7-OGT, whereas GT specific to position 2' or 4' in chalcones or 2' in dihydrochalcones cluster separately (FIG. 2).

The MdPh-4'-OGT sequence displayed 99 fry identity to the predicted anthocyanidin 5,3-OGT from *M. domestica*, 95% identity to the flavonoid 7-OCT from *P. communis* and 89% identity to crocetin CT from *P. bretschneideri*. MdPh-4'-OGT had significantly lower identity, 33%, to *A. majus* chalcone 4'-OGT [Ono et al. (2006), supra], and 28% to phloretin 2'-OGT from *M. pumila* [Jugde H. et al. (2008), supra] and *M. domestica* [Gosch C. et al. (2010), supra], respectively.

Example 2

Expression and Biochemical Characterization of the dPh-4'-OGT Protein

Bacterial cells expressing MdPh-4'-OGT were harvested and lysed, and the recombinant His-tagged MdPh-4'-OGT protein was purified by a nickel affinity column and visualized by SDS-PAGE (FIG. 9). The predicted MdPh-4'-OGT protein sequence consisted of 481 amino acids, with a calculated molecular mass of 53.4 kDa, in agreement with the mobility observed in SDS-PAGE (FIG. 9), and a theoretical isoelectric point of 4.9.

For functional characterization of MdPh-4'-OGT, aliquots of the His-tagging and affinity chromatography to purify *E. coli*-expressed protein were assayed for glycosyltransferase activity using phloretin as the substrate and UDP-glucose as the sugar donor. Products formed by the recombinant MdPh-4'-OGT protein were analyzed by LC-MS and compared with those for phloretin, trilobatin and phloridzin standards (FIGS. 3A-H). The product of MdPh-4'-OGT catalysis on phloretin substrate was observed at 4.8 minutes, which is the same retention time as the trilobatin standard (FIGS. 3A-H). An LC-MS run where the trilobatin standard was spiked into the MdPh-4'-OGT reaction mixture further confirmed that the product of the reaction had identical retention time (data not shown). Assays containing heat-inactivated MdPh-4'-OGT protein or assays without UDP-glucose as a co-substrate displayed no detectable GT activity with any of the substrates tested in this study (FIGS. 3A-H).

The present inventor tested the purified recombinant MdPh-4'-OGT activity on a wide array of potential substrates such as trilobatin (illustrated by no. 6 in FIGS. 1 and 4), phloridzin (illustrated by no. 7 in FIG. 4), quercetin (illustrated by no. 8 in FIG. 4), naringenin (illustrated by no. 9 in FIG. 4), epicatechin (illustrated by no. 10 in FIG. 4), cyanidin (illustrated by no. 11 in FIG. 4), 4-coumaric acid (illustrated by no. 12 in FIG. 4), and caffeic acid (illustrated by no. 13 in FIG. 4) that are natural constitutes of apple fruits to determine substrate preference. Also, since the 4' position of dihydrochalcone/chalcones corresponds to the 7 position of flavonoids quercetin, naringenin, epicatechin, it could be assumed that the aglycones of the 7-O-glycosylated is flavonoid are also native substrates.

MdPh-4'-OGT enzyme had the highest activity on phloretin (illustrated by no. 5 in FIGS. 1 and 4) substrate (FIG. 4). Incubation of trilobatin and phloridzin with purified MdPh-4'-OGT led to the production of the corresponding di-O-glucosides (FIGS. 10A-F). Incubation of naringenin with purified MdPh-4'-OGT led to the formation of the corresponding naringenin-7-O-glucoside (FIGS. 11A-E). On the other hand, incubation of quercetin with purified MdPh-4'-OGT led to the production of three different products in vitro, only one of which could be identified as quercetin-7-O-glucosid (FIGS. 12A-D). Also, it was surprising that three products were formed because in general glycosyltransferases are rather regio-selective concerning the glycosylation site. The MdPh-4'-OGT enzyme was tested with the chalcone butein (illustrated by no. 14 in FIG. 4) in the presence of UDP-glucose as the sugar donor. These enzyme reactions led to the production of the corresponding O-glucoside (data not shown). Although the exact nature of the glycosylation in these reactions has not been determined, the MS spectra clearly indicated that the sugar molecules were attached to trilobatin, phloridzin, quercetin, and butein, respectively; NMR could be used to confirm the regio-specificity of the glycosylation and to clarify the nature of the glycosylated products trilobatin, phloridzin, quercetin, and butein obtained using UDP-glucose as the sugar donor.

In contrast, no products were detected with epicatechin, cyanidin, 4-coumaric acid, and caffeic acid under standard test conditions (FIG. 4).

For characterization of general kinetic parameters, the present inventor used the His-tagged, affinity chromatography-purified MdPh-4'-OGT protein (Table 1, below, and FIGS. 5A-D). Kinetic parameters were determined for MdPh-4'-OGT with respect to phloretin and UDP-glucose. The $K_m$ of MdPh-4'-OGT with phloretin was 26.11±6.97 µM, with a $V_{max}$ of 1.86±0.30 pkat·µg$^{-1}$ proteins (FIG. 5A). The observed $K_m$ for UDP-glucose was 1.19±0.27 µM, with a $V_{max}$ of 1.77±0.34 pkat µg$^{-1}$ proteins (FIG. 5B). MdPh-4'-OGT enzyme activity was tested over a pH range of 4.0-10.0. The enzyme showed significant activity from pH 7.0-9.0 with maximum activity at pH 9.0. Activity decreased to 17% at pH 6.0 and less than 5% at pH 10.0 (FIG. 5C). Maximum turnover rate was reached at 50° C. (FIG. 5D), with a calculated activation energy of 18.28 kJ/mol.

TABLE 1

Kinetic parameters of apple MdPh-4'-OGT, obtained with His-tagging and affinity chromatography purified protein

| Substrate | Km (µM) | Vmax (pkat µg$^{-1}$ protein) | kcat (s$^{-1}$) (×10$^{-2}$) | kcat/Km (µM$^{-1}$s$^{-1}$) (×10$^{-3}$) |
|---|---|---|---|---|
| Phloretin | 26.11 ± 6.97 | 1.86 ± 0.30 | 9.94 ± 1.23 | 3.81 |
| UDP-glucose | 1.19 ± 0.27 | 1.77 ± 0.34 | 9.43 ± 0.58 | 79.24 |

The divalent cations $Mg^{2+}$, $Mn^{2+}$ and the monovalent cations $Ca^+$, $K^+$ did not affect enzyme activity, suggesting that they are not required as co-factors. The MdPh-4'-OGT enzyme was tested with phloretin in the presence of an additional activated sugar donor, UDP-galactose. This reaction displayed no detectable GT activity with UDP-galactose as a co-substrate (data not shown). In contrast, MdPGT1 could glycosylates phloretin in the presence of three sugar donors: UDP-glucose, UDP-galactose, and UDP-xylose [Jugde et al. (2008), supra].

These apparent kinetic values for the substrate, phloretin, were within the range observed for other plant glucosyltransferase [Jugde et al. (2008), supra; Gosch C. et al., *Trees* (2012) 26: 259-271]. However, *Malus* Ph-2'-OGT [Gosch C. et al. (2010), supra] showed 3 times higher Km for phloretin than MdPh-4'OGT, whereas MdPGT1 [Jugde et al. (2008), supra] showed a 41 times lower Km and, thus, a higher affinity of the glucosyltransferase for phloretin than MdPh-4'-OGT.

In general, glycosyltransferases are known as a supergene family with low sequence similarity and only few highly conserved regions. They are described as predominantly region selective or region-specific concerning the sugar attachment site but usually not highly substrate-specific. The glycosylated product of phloretin and UDP-glucose co-migrated with a known trilobatin standard, indicating that MdPh-4'-OGT is likely to be an enzyme that glycosylates phloretin to trilobatin in planta. Also, different plant species, including apples, have been reported to produce several phloretin derivatives, such as trilobatin, phloridzin, and sieboldin (3-hydroxyphloretin4-O-glucoside).

Example 3

Spatial Expression of MdPh-4'-OGT

The level of expression of the MaPh-4'-OGT gene was examined by qRT-PCR on leaf, flower and fruit tissues of *M. domestica* "Golden delicious" using actin as a reference gene. Transcripts of MaPh-4'-OGT gene were detected in the flower, leaf and fruit (skin and flesh) samples, but the expression level varied statistically between tissues, especially during fruit development (FIG. 6). The expression level of MdPh-4'-OGT transcript was higher in young leaves than those found in mature leaves, in the flowers, and in the fruits (skin and flesh), which was consistent with the high levels of trilobatin found in young leaves of different *Malus* species.

The lowest level of MdPh-4'-OGT gene transcript was observed in the flower and in the flesh of fruit stage 3. The expression data indicate that the apple MdPh-4'-OGT transcript is expressed in a wide range of tissues and can be found in all tissues where different dihydrochalcones have been previously reported.

Additional GT gene transcript analysis, enzyme characterization, and subsequent targeted gene silencing are carried out to provide a better understanding of the *Malus* GT genes in trilobatin dihydrochalcone biosynthesis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of producing trilobatin, the method comprising contacting a polypeptide comprising an amino acid sequence at least 98% identical to SEQ ID NO: 8 and having a 4'-0-glycosyltransferase activity with phloretin and UDP-glucose under conditions which allow the formation of trilobatin, thereby producing trilobatin, and purifying said trilobatin, wherein said polypeptide is exogenously expressed in a plant cell, a bacterial or a yeast cell.

2. The method of claim 1, wherein the formation of trilobatin is effected in vivo.

3. The method of claim 2, wherein said in vivo is in a plant cell.

4. The method of claim 1, wherein said amino acid sequence is at least 99% identical to SEQ ID NO: 8.

5. The method of claim 1, wherein said amino acid sequence is SEQ ID NO: 8.

6. The method of claim 2, wherein said in vivo is in a bacterial or yeast cell.

7. A method of producing trilobatin, the method comprising transforming a plant cell, a bacterial cell or a yeast cell, with a polynucleotide encoding a polypeptide comprising an amino acid sequence at least 98% identical to SEQ ID NO: 8 and having a 4'-0-glycosyltransferase activity, thereby exogenously expressing said polypeptide in a plant cell, contacting said polypeptide with phloretin and UDP-glucose under conditions which allow the formation of trilobatin, producing trilobatin in said plant cell, bacterial cell or yeast cell, and purifying said trilobatin.

* * * * *